(12) United States Patent
Stürmer et al.

(10) Patent No.: US 8,227,218 B2
(45) Date of Patent: Jul. 24, 2012

(54) METHOD FOR THE ENZYMATIC REDUCTION OF ALKYNE DERIVATES

(75) Inventors: Rainer Stürmer, Rödersheim-Gronau (DE); Bernhard Hauer, Fussgönheim (DE); Bettina Rosche, Randwick (AU); André Mueller, Vienna (AT)

(73) Assignee: BASF SE, Ludwigshafen (DE)

( * ) Notice: Subject to any disclaimer, the term of this patent is extended or adjusted under 35 U.S.C. 154(b) by 614 days.

(21) Appl. No.: 12/439,427

(22) PCT Filed: Aug. 30, 2007

(86) PCT No.: PCT/EP2007/059071
§ 371 (c)(1),
(2), (4) Date: Feb. 27, 2009

(87) PCT Pub. No.: WO2008/025831
PCT Pub. Date: Mar. 6, 2008

(65) Prior Publication Data
US 2010/0009421 A1     Jan. 14, 2010

(30) Foreign Application Priority Data

Sep. 1, 2006   (EP) .................................... 06120008

(51) Int. Cl.
*C12P 7/26*     (2006.01)

(52) U.S. Cl. .... 435/148; 435/171; 435/189; 435/254.21
(58) Field of Classification Search ................... 435/148, 435/189, 254.21, 171
See application file for complete search history.

(56) References Cited

U.S. PATENT DOCUMENTS
6,596,520 B1   7/2003  Friedrich et al.

FOREIGN PATENT DOCUMENTS
DE   10019377 A1   10/2001
EP    1069183 A2    1/2001
EP    1149849 A1   10/2001

OTHER PUBLICATIONS

Genbank entry for S. cerevisiae Genbank Q03558 from http://exon.ucsc.edu/cgi-bin/hgGene?hgg_gene=YHR179W&hgg_chrom=chr8&hgg_start=462497&hgg_end=463700&hgg_type=sgdGene&db=sacCer1&hgsid=10398 downloaded Sep. 27, 2011.*
Definition of independent from http://www.merriam-webster.com/dictionary/independent downloaded Sep. 27, 2011.*
Lou et al. Enzyme Microbial Technol. (2004) 35: 190-196.*
McKenzie et al. Gut (1990) 31: 536-538.*
van Dijken et al. J. Bacteriology (2002) 184(3): 672-678.*
Muller et al. Angew. Chem. Int. Ed. (Apr. 27, 2007) 46: 3316-3318.*
Brown et al. J. Biol. Chem. (1999) 273(49): 32753-32762.*
Takeshita et al. Res. Comm. Molecular Pathology and Pharmacology (1995) 88(1): 123-126.*
Niino et al. J. Biol. Chem. (1995) 270(5): 1983-1991.*
Takeshita, M., et al., "Asymmetric biotransformation of phenyl-C4 derivatives in rat liver (S-9) and baker's yeast," Journal or Molecular Catalysis B: Enzymatic 5, pp. 245-248 (1998).

* cited by examiner

*Primary Examiner* — Susan Hanley
(74) *Attorney, Agent, or Firm* — Connolly Bove Lodge & Hutz LLP

(57) ABSTRACT

The invention relates to a method for the enzymatic reduction of alkyne derivatives of the formula (1), $$R^1-\!\!\!\equiv\!\!\!-\underset{R^2}{\overset{O}{\|}}\!\!C \longrightarrow R^1\!\!\sim\!\!\!=\!\!\!\sim\!\!\underset{R^2}{\overset{O}{\|}}\!\!C$$

(1)                                  (2)

wherein $R^1$ represents H, $C_1$-$C_6$-alkyl, $C_2$-$C_6$-alkenyl, or an optionally substituted carbocyclic or heterocyclic, aromatic or non-aromatic group, $R^2$ represents H, $C_1$-$C_6$-alkyl, $C_2$-$C_6$-alkenyl, by reaction in the presence of special reductases.

9 Claims, 7 Drawing Sheets

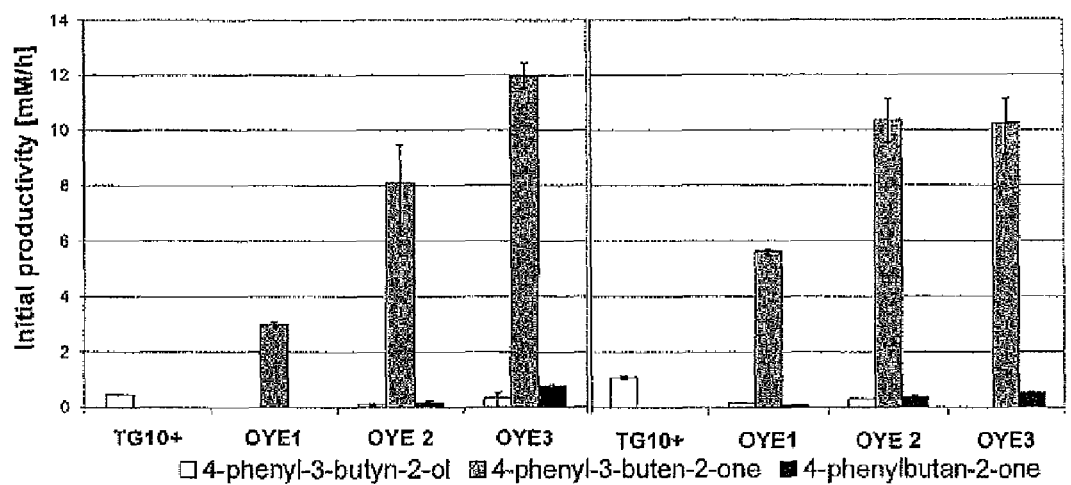
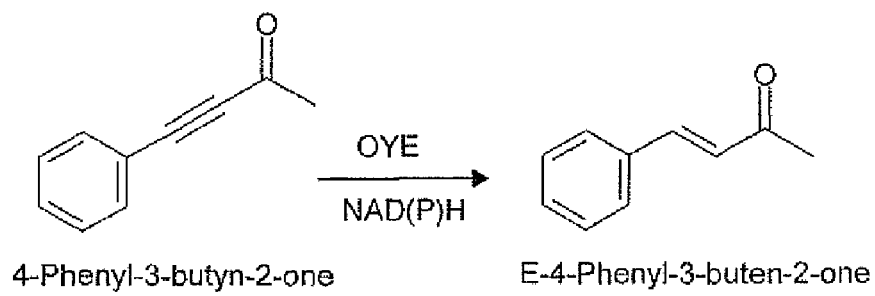
Fig. 1

OYE 1: Saccharomyces carlsbergensis (Genbank Q02899) (SEQ ID NO: 1)

```
SFVKDFKPQA LGDTNLFKPI KIGNNELLHR AVIPPLTRMR ALHPGNIPWR DWAVEYYTQR
AQRPGTMIIT EGAFISPQAG GYDNAPGVWS EEQMVEWTKI FNAIHEKKSF VWVQLWVLGW
AAFPDNLARD GLRYDSASDN VFMDAEQEAK AKKANNPQHS LTKDEIKQYI KEYVQAAKNS
IAAGADGVEI HSANGYLLNQ FLDPHSNTRT DEYGGSIENR ARFTLEVVDA LVEAIGHEKV
GLRLSPYGVF NSMSGGAETG IVAQYAYVAG ELEKRAKAGK RLAFVHLVEP RVTNPFLTEG
EGEYEGGSND FVYSIWKGPV IRAGNFALHP EVVREEVKDK RTLIGYGRFF ISNPDLVDRL
EKGLPLNKYD RDTFYQMSAH GYIDYPTYEE ALKLGWDKK
```

OYE 2: Saccharomyces cerevisiae (Genbank Q03558) (SEQ ID NO: 2)

```
PFVKDFKPQA LGDTNLFKPI KIGNNELLHR AVIPPLTRMR AQHPGNIPNR DWAVEYYAQR
AQRPGTLIIT EGTFPSPQSG GYDNAPGIWS EEQIKEWTKI FKAIHENKSF AWVQLWVLGW
AAFPDTLARD GLRYDSASDN VYMNAEQEEK AKKANNPQHS ITKDEIKQYV KEYVQAAKNS
IAAGADGVEI HSANGYLLNQ FLDPHSNNRT DEYGGSIENR ARFTLEVVDA VVDAIGPEKV
GLRLSPYGVF NSMSGGAETG IVAQYAYVLG ELERRAKAGK RLAFVHLVEP RVTNPFLTEG
EGEYNGGSNK FAYSIWKGPI IRAGNFALHP EVVREEVKDP RTLIGYGRFF ISNPDLVDRL
EKGLPLNKYD RDTFYKMSAE GYIDYPTYEE ALKLGWDKN
```

OYE 3: Saccharomyces cerevisiae (Genbank P41816) (SEQ ID NO: 3)

```
PFVKGFEPIS LRDTNLFEPI KIGNTQLAHR AVMPPLTRMR ATHPGNIPNK EWAAVYYGQR
AQRPGTMIIT EGTFISPQAG GYDNAPGIWS DEQVAEWKNI FLAIHDCQSF AWVQLWSLGW
ASFPDVLARD GLRYDCASDR VYMNATLQEK AKDANNLEHS LTKDDIKQYI KDYIHAAKNS
IAAGADGVEI HSANGYLLNQ FLDPHSNKRT DEYGGTIENR ARFTLEVVDA LIETIGPERV
GLRLSPYGTF NSMSGGAEPG IIAQYSYVLG ELEKRAKAGK RLAFVHLVEP RVTDPSLVEG
EGEYSEGTND FAYSIWKGPI IRAGNYALHP EVVREQVKDP RTLIGYGRFF ISNPDLVYRL
EEGLPLNKYD RSTFYTMSAE GYTDYPTYEE AVDLGWNKN
```

Fig. 2

METHOD FOR THE ENZYMATIC REDUCTION OF ALKYNE DERIVATES

PRIOR ART

No methods for the enzymatic reduction of alkyne derivatives requiring no ATP have been disclosed to date.

Takeshita, M. et al. describe in *Journal of Molecular Catalysis* B: Enzymatic 5 (1998) 245-248 experiments on the asymmetric biotransformation of phenyl-$C_4$ derivatives with the S-9 rat liver fraction and with baker's yeast. According to this, 4-phenyl-3-butyn-2-one is not significantly converted into the corresponding buten-2-one by the rat liver fraction compared with the control. Experiments with whole yeast cells also yielded an insignificant amount (3% yield) of buten-2-one. There was on the other hand formation, as main component, of the corresponding S-butan-2-ol (31%), the corresponding butan-2-one (8%) and the corresponding S-butyn-2-ol (5%). It was not possible to assign particular enzyme activities to these biotransformations, because the experiments were carried out with whole yeast cells. In addition, the experiments necessarily took place in the presence of cellular cofactors such as, for example, ATP.

The object was to provide a method for the enzymatic reduction of alkyne derivatives requiring no ATP.

BRIEF DESCRIPTION OF THE INVENTION

The above object has been achieved by using the reductases OYE 1, 2 and 3 and functional equivalents thereof for reducing alkyne derivatives of the general formula (1).

DESCRIPTION OF THE FIGURES

The appended figures show

FIG. 1 the biotransformation of 20 mM 4-phenyl-3-butyn-2-one with OYE 1-3 in the presence of NADPH (left) or NADH (right), EDTA and isopropanol at pH 6.8 and 30° C. after 1 h. The enzymes were overexpressed in *E. coli* TG10+; TG10+ itself served as control;

FIG. 2 the amino acid sequences of the enzymes OYE 1, 2 and 3 used;

DETAILED DESCRIPTION OF THE INVENTION

Figure 3:
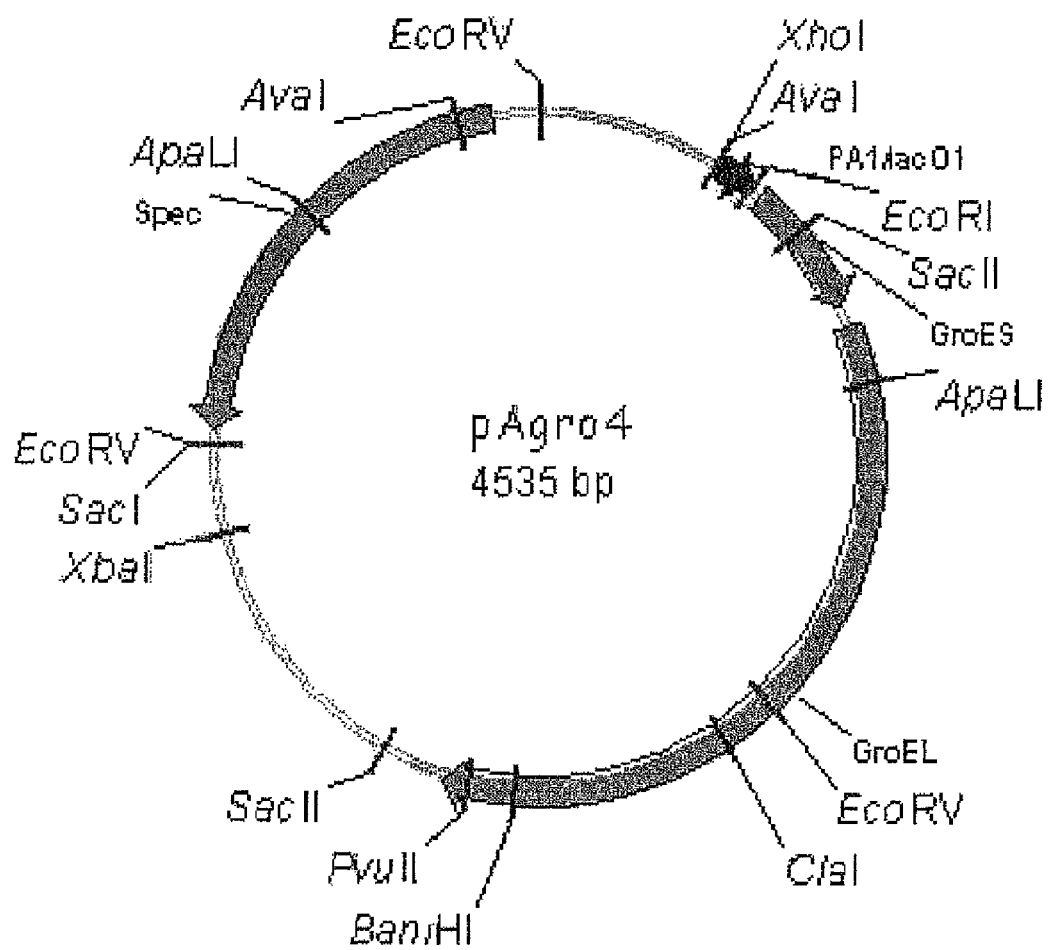
FIG. 3 the plasmid map of pAgro4.

The present invention relates to a method for the enzymatic preparation of alkenone derivatives of the general formula (2) from α,β-unsaturated alkynone derivatives of the general formula (1)

in which $R^1$ is H, $C_1$-$C_6$-alkyl, $C_2$-$C_6$-alkenyl, or an optionally substituted carbo- or heterocyclic aromatic or nonaromatic ring, and $R^2$ is H, $C_1$-$C_8$-alkyl or $C_2$-$C_6$-alkenyl, by reducing a compound of the formula (1) in the presence of a reductase (i) comprising at least one of the polypeptide sequences SEQ ID NO:1, 2, 3, 5, 7 or 9 or (ii) with a functionally equivalent polypeptide sequence which has at least 80% sequence identity with SEQ ID NO:1, 2, 3, 5, 7 or 9.

The invention preferably provides in particular the E configuration of compounds of the formula 2 in which $R^1$ and $R^2$ have the abovementioned meanings. The compounds of the formula 2 are in particular more than 50%, in particular more than 60, 70 or 80%, but preferably more than 90% such as, for example, 95 to 99%, in particular about 100%, in the form with the E configuration.

The method of the invention can in principle be carried out both with purified or enriched enzyme itself and with microorganisms which express this enzyme naturally or recombinantly, with cell homogenates derived therefrom or, if the microorganism secretes the enzyme into the surroundings, with culture supernatant. In particular, however, an "enzymatic reaction" comprises in the context of the invention a reaction in an essentially ATP-free environment, i.e. preferably a reaction with cell-free enzyme preparations such as pure or enriched enzymes or suitable protein fractions which no longer comprise any low molecular weight cellular constituents such as, in particular, ATP.

Unless stated otherwise, the meanings are:

$C_1$-$C_6$-alkyl in particular methyl, ethyl, propyl, butyl, pentyl or hexyl, and the corresponding analogues which are branched one or more times, such as i-propyl, i-butyl, sec-butyl, tert-butyl, i-pentyl or neopentyl, with preference in particular for said $C_1$-$C_4$-alkyl radicals;

$C_2$-$C_6$-alkenyl in particular the monounsaturated analogues of the abovementioned alkyl radicals having 2 to 6 carbon atoms, with preference in particular for the corresponding $C_2$-$C_4$-alkenyl radicals.

Carbo- and heterocyclic aromatic or nonaromatic rings in particular optionally fused rings having 3 to 12 carbon atoms and optionally 1 to 4 heteroatoms such as N, S and O, in particular N or O. Examples which may be mentioned are cyclopropyl, cyclobutyl, cyclopentyl, cyclohexyl, cycloheptyl, the mono- or polyunsaturated analogues thereof such as cyclobutenyl, cyclopentenyl, cyclohexenyl, cycloheptenyl, cyclohexadienyl, cycloheptadienyl; phenyl and naphthyl; and 5- to 7-membered saturated or unsaturated heterocyclic radicals having 1 to 4 heteroatoms which are selected from O, N and S, where the heterocycle may optionally be fused to further heterocycle or carbocycle. Mention should be made in particular of heterocyclic radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, coumarone, indole and quinoline. The cyclic radicals, but also the abovementioned alkyl and alkenyl radicals, may optionally be substituted one or more times, such as, for example, 1, 2 or 3 times. Mention should be made as example of suitable substituents of: halogen, in particular F, Cl, Br; —OH, —SH, —$NO_2$, —$NH_3$, —$SO_3H$, $C_1$-$C_4$-alkyl and $C_2$-$C_4$-alkenyl, $C_1$-$C_4$- alkoxy; and hydroxy-$C_1$-$C_4$-alkyl; where the alkyl and alkenyl radicals are as defined above, and the alkoxy radicals are derived from the above-defined corresponding alkyl radicals.

The method of the invention can be carried out in particular with alkynes of the general formula (1) in which $R^1$ is $C_1$-$C_4$-alkyl in branched and unbranched form, $C_2$-$C_6$-alkenyl in branched and unbranched form or optionally substituted phenyl.

Particularly suitable substrates for the method of the invention are those alkynes of the general formula (1) in which $R^1$ is optionally substituted phenyl, and $R^2$ is $CH_3$.

The reductases used according to the invention in some cases occasionally reduce not only the triple bond in the α,β position relative to the carbonyl function but also the carbonyl function itself, the corresponding alcohol then being formed thereby. It is likewise possible for the alkenes to be partly reduced further to the corresponding alkane.

Reductases suitable for the method of the invention are all enzymes able to reduce 4-phenyl-3-butyn-2-one in an NAD(P)H-dependent and preferably ATP-independent reaction to E-4-phenyl-3-buten-2-one. This reaction is also called model reaction hereinafter.

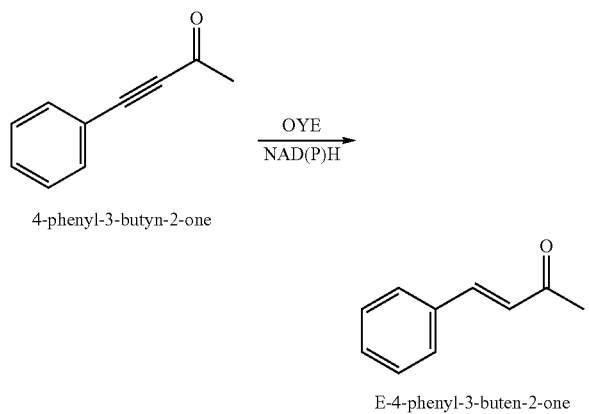

In addition, the reductases suitable for the method of the invention (which are occasionally also referred to as enoate reductases) have a polypeptide sequence as shown in SEQ ID NO:1, 2, 3, 5, 7 or 9 or a polypeptide sequence which has at least 80% such as, for example, at least 90%, or at least 95% and in particular at least 97%, 98% or 99% sequence identity with SEQ ID NO: 1, 2, 3, 5, 7 or 9.

A polypeptide having SEQ ID NO:1 is known under the name OYE1 from *Saccharomyces carlsbergensis* (Genbank Q02899).

A polypeptide having SEQ ID NO:2 is encoded by the OYE2 gene from baker's yeast (*Saccharomyces cerevisiae* gene locus YHR179W) (Genbank Q03558).

A polypeptide having SEQ ID NO:3 is encoded by the OYE3 gene from baker's yeast (*Saccharomyces cerevisiae* gene locus YPL171C) (Genbank P 41816).

The sequences shown in SEQ ID NO: 5, 7 and 9 correspond to SEQ ID NO: 1, 2 and 3 and differ therefrom only by an additional N-terminal methionine residue.

The sequence identity is to be ascertained for the purposes described herein by the "GAP" computer program of the Genetics Computer Group (GCG) of the University of Wisconsin, and the version 10.3 using the standard parameters recommended by GCG is to be employed.

Such reductases can be obtained starting from SEQ ID NO: 1, 2, 3, 5, 7 or 9 by targeted or randomized mutagenesis methods known to the skilled worker. An alternative possibility is, however, also to search in microorganisms, preferably in those of the genera *Alishewanella, Alterococcus, Aquamonas, Aranicola, Arsenophonus, Azotivirga, Brenneria, Buchnera* (aphid P-endosymbionts), *Budvicia, Buttiauxella, Candidatus Phlomobacter, Cedecea, Citrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia* or *Yokenella*, for reductases which catalyze the above-mentioned model reaction and whose amino acid sequence already has the required sequence identity to SEQ ID NO: 1, 2, 3, 5, 7 or 9 or is obtained by mutagenesis methods.

The reductase can be used in purified or partly purified form or else in the form of the microorganism itself. Methods for obtaining and purifying dehydrogenases from microorganisms are well known to the skilled worker.

The enantioselective reduction with the reductase preferably takes place in the presence of a suitable cofactor (also referred to as cosubstrate). Cofactors normally used for reduction of the ketone are NADH and/or NADPH. Reductases can moreover be employed as cellular systems which inherently comprise cofactor, or alternative redox mediators can be added (A. Schmidt, F. Hollmann and B. Bühler "Oxidation of Alcohols" in K. Drauz and H. Waldmann, Enzyme Catalysis in Organic Synthesis 2002, Vol. III, 991-1032, Wiley-VCH, Weinheim).

The enantioselective reduction with the reductase additionally preferably takes place in the presence of a suitable reducing agent which regenerates cofactor oxidized during the reduction. Examples of suitable reducing agents are sugars, in particular hexoses such as glucose, mannose, fructose, and/or oxidizable alcohols, especially ethanol, propanol or isopropanol, and formate, phosphite or molecular hydrogen. To oxidize the reducing agent and, associated therewith, to regenerate the coenzyme it is possible to add a second dehydrogenase such as, for example, glucose dehydrogenase when glucose is used as reducing agent, or formate dehydrogenase when formate is used as reducing agent. This can be employed as free or immobilized enzyme or in the form of free or immobilized cells. Preparation thereof can take place either separately or by coexpression in a (recombinant) reductase strain.

A preferred embodiment of the claimed method is to regenerate the cofactors by an enzymatic system in which a second dehydrogenase, particularly preferably a glucose dehydrogenase, is used.

It may further be expedient to add further additions promoting the reduction, such as, for example, metal salts or chelating agents such as, for example, EDTA.

The reductases used according to the invention can be employed free or immobilized. An immobilized enzyme means an enzyme which is fixed to an inert carrier. Suitable carrier materials and the enzymes immobilized thereon are disclosed in EP-A-1149849, EP-A-1 069 183 and DE-A 10019377, and the references cited therein. The disclosure of these publications in this regard is incorporated in its entirety herein by reference. Suitable carrier materials include for example clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The carrier materials are normally employed in a finely divided particulate form to prepare the carrier-bound enzymes, with preference for porous forms. The particle size of the carrier material is normally not more than 5 mm, in particular not more than 2 mm (grading curve). It is possible analogously to choose a free or immobilized form on use of the dehydrogenase as whole-cell catalyst. Examples of carrier materials are Ca alginate and carrageenan. Both enzymes and cells can also be crosslinked directly with glutaraldehyde (crosslinking to give CLEAs). Corresponding and further immobilization methods are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

The reaction can be carried out in aqueous or nonaqueous reaction media or in 2-phase systems or (micro)emulsions. The aqueous reaction media are preferably buffered solutions which ordinarily have a pH of from 4 to 8, preferably from 5 to 8. The aqueous solvent may, besides water, additionally comprise at least one alcohol, e.g. ethanol or isopropanol, or dimethyl sulfoxide.

Nonaqueous reaction media mean reaction media which comprise less than 1% by weight, preferably less than 0.5% by weight, of water based on the total weight of the liquid reaction medium. The reaction can in particular be carried out in an organic solvent.

Suitable organic solvents are for example aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, tetrachloroethane, dichloroethane or tetrachloroethane, aromatic hydrocarbons such as benzene, toluene, the xylenes, chlorobenzene or dichlorobenzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. The aforementioned ethers, especially tetrahydrofuran, are particularly preferably used.

The reduction with reductase can for example be carried out in an aqueous organic reaction medium such as, for example, water/isopropanol in any mixing ratio such as, for example, 1:99 to 99:1 or 10:90 to 90:10, or an aqueous reaction medium.

The substrate (1) is preferably employed in the enzymatic reduction in a concentration from 0.1 g/l to 500 g/l, particularly preferably from 1 g/l to 50 g/l, and can be fed in continuously or discontinuously.

The enzymatic reduction ordinarily takes place at a reaction temperature below the deactivation temperature of the reductase employed and above −10° C. It is particularly preferably in the range from 0 to 100° C., in particular from 15 to 60° C. and specifically from 20 to 40° C., e.g. at about 30° C.

A possible procedure for example is to mix the substrate (1) with the reductase, the solvent and, if appropriate, the coenzymes, if appropriate a second dehydrogenase to regenerate the coenzyme and/or further reducing agents, thoroughly, e.g. by stirring or shaking. However, it is also possible to immobilize the reductase in a reactor, for example in a column, and to pass a mixture comprising the substrate and, if appropriate, coenzymes and/or cosubstrates through the reactor. For this purpose it is possible to circulate the mixture through the reactor until the desired conversion is reached.

In this case, the triple bond in the $\alpha,\beta$ position to the carbonyl function is reduced to the double bond, and occasionally there is also reduction of the carbonyl function itself to the alcohol function. The reduction is ordinarily carried out until the conversion is at least 70%, particularly preferably at least 85% and in particular at least 95%, based on the substrate present in the mixture. The progress of the reaction, i.e. the sequential reduction of the double bond, can moreover be followed by conventional methods such as gas chromatography or high pressure liquid chromatography.

"Functional equivalents" or analogues of the specifically disclosed enzymes are in the context of the present invention polypeptides which differ therefrom and which still have the desired biological activity such as, for example, substrate specificity. Thus, "functional equivalents" mean for example enzymes which catalyze the model reaction and which have at least 20%, preferably 50%, particularly preferably 75%, very particularly preferably 90% of the activity of an enzyme comprising one of the amino acid sequences listed under SEQ ID NO:1, 2 or 3. Functional equivalents are additionally preferably stable between pH 4 to 10 and advantageously have a pH optimum between pH 5 and 8 and a temperature optimum in the range from 20° C. to 80° C.

"Functional equivalents" also mean according to the invention in particular mutants which have an amino acid other than that specifically mentioned in at least one sequence position of the abovementioned amino acid sequences but nevertheless have one of the abovementioned biological activities. "Functional equivalents" thus comprise the mutants obtainable by one or more amino acid additions, substitutions, deletions and/or inversions, it being possible for said modifications to occur in any sequence position as long as they lead to a mutant having the property profile according to the invention. Functional equivalents also exist in particular when the reactivity patterns agree qualitatively between mutant and unmodified polypeptide, i.e. for example identical substrates are converted at a different rate.

Examples of suitable amino acid substitutions are to be found in the following table:

| Original residue | Substitution examples |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the described polypeptides and "functional derivatives".

"Precursors" are in this connection natural or synthetic precursors of the polypeptides with or without the desired biological activity.

"Functional derivatives" of polypeptides of the invention can likewise be prepared on functional amino acid side groups or on their N- or C-terminal end with the aid of known techniques. Such derivatives comprise for example aliphatic esters of carboxylic acid groups, amides of carboxylic acid groups, obtainable by reaction with ammonia or with a primary or secondary amine; N-acyl derivatives of free amino groups prepared by reaction with acyl groups; or O-acyl derivatives of free hydroxy groups prepared by reaction with acyl groups.

In the case where protein glycosylation is possible, "functional equivalents" of the invention comprise proteins of the type designated above in deglycosylated or glycosylated form, and modified forms obtainable by altering the glycosylation pattern.

"Functional equivalents" of course also comprise polypeptides which are obtainable from other organisms, and naturally occurring variants. For example, it is possible to establish ranges of homologous sequence regions by comparison of sequences, and to ascertain equivalent enzymes based on the specific requirements of the invention.

"Functional equivalents" likewise comprise fragments, preferably individual domains or sequence motifs, of the polypeptides of the invention, which have, for example, the desired biological function.

"Functional equivalents" are additionally fusion proteins which comprise one of the abovementioned polypeptide sequences or functional equivalents derived therefrom and at least one further, heterologous sequence which is functionally different therefrom and is functional N- or C-terminal linkage (i.e. with negligible mutual functional impairment of the parts of the fusion protein). Nonlimiting examples of such heterologous sequences are, for example, signal peptides or enzymes.

Homologues of the proteins of the invention can be identified by screening combinatorial libraries of mutants, such as, for example, truncation mutants. For example, a variegated library of protein variants can be generated by combinatorial mutagenesis at the nucleic acid level, such as, for example, by enzymatic ligation of a mixture of synthetic oligonucleotides. There is a large number of methods which can be used to prepare libraries of potential homologues from a degenerate oligonucleotide sequence. Chemical synthesis of a degenerate gene sequence can be carried out in an automatic DNA synthesizer, and the synthetic gene can then be ligated into a suitable expression vector. Use of a degenerate set of genes makes it possible to provide all the sequences which encode the desired set of potential protein sequences in one mixture. Methods for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques are known in the art for screening gene products of combinatorial libraries which have been prepared by point mutations or truncation, and for screening cDNA libraries for gene products having a selected property. These techniques can be adapted to the rapid screening of gene libraries which have been generated by combinatorial mutagenesis of homologues of the invention. The most commonly used techniques for screening large gene libraries, which are subject to high-throughput allows this, include the cloning of the gene library into replicable expression vectors, transformation of suitable cells with the resulting vector library and expression of the combinatorial genes under conditions under which detection of the desired activity facilitates isolation of the vector which encodes the gene whose product has been detected. Recursive ensemble mutagenesis (REM), a technique which increases the frequency of functional mutants in the libraries, can be used in combination with the screening tests to identify homologues (Arkin and Yourvan (1992) PNAS 89:7811-7815; Delgrave et al. (1993) Protein Engineering 6(3):327-331).

The invention further relates to nucleic acid sequences (single- and double-stranded DNA and RNA sequences such as, for example, cDNA and mRNA) which code for an enzyme having reductase activity according to the invention. Nucleic acid sequences which code for example for amino acid sequences shown in SEQ ID NO:1, 2 or 3 or characteristic partial sequences thereof are preferred.

All nucleic acid sequences mentioned herein can be prepared in a manner known per se by chemical synthesis from the nucleotide building blocks, such as, for example, by fragment condensation of individual overlapping complementary nucleic acid building blocks of the double helix. Chemical synthesis of oligonucleotides can take place for example in a known manner by the phosphoramidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods are described in Sambrook et al. (1989), Molecular Cloning: A laboratory manual, Cold Spring Harbor Laboratory Press.

Further embodiments for carrying out the enzymatic reduction method of the invention:

The reductases employed according to the invention can be used in the method of the invention as free or immobilized enzyme.

The pH in the method of the invention is advantageously kept between pH 4 and 12, preferably between pH 4.5 and 9, particularly preferably between pH 5 and 8.

It is possible to use for the method of the invention growing cells which comprise nucleic acids, nucleic acid constructs or vectors coding for the reductase. It is also possible to use resting or disrupted cells. Disrupted cells mean for example cells which have been made permeable by a treatment with, for example, solvents, or cells which have been disintegrated by an enzyme treatment, by mechanical treatment (e.g. French press or ultrasound) or by any other method. The crude extracts obtained in this way are advantageously suitable for the method of the invention. Purified or partially purified enzymes can also be used for the method. Immobilized microorganisms or enzymes are likewise suitable and can advantageously be used in the reaction.

The method of the invention can be carried out batchwise, semi-batchwise or continuously.

The method can advantageously be carried out in bioreactors as described for example in biotechnology, Vol. 3, 2nd edition, Rehm et al., editors (1993, especially chapter II.

The following examples are intended to illustrate the invention without, however, restricting it. Reference is made to the appended figures in this connection.

Experimental Section

EXAMPLE 1

Preparation of the Reductase-Expressing *E. Coli* TG10+Transformants and of the Corresponding Transformation Constructs Unless stated otherwise, the cloning steps carried out in the context of the present invention, such as, for example, restriction cleavages, agarose gel electrophoresis, purification of DNA fragments, transfer of nucleic acids to nitrocellulose and nylon membranes, linkage of DNA fragments, transformation of microorganisms, culturing of microorganisms, replication of phages and sequence analysis of recombinant DNA, can be carried out as described in Sambrook et al., (1989), loc. cit.

Figure 4:
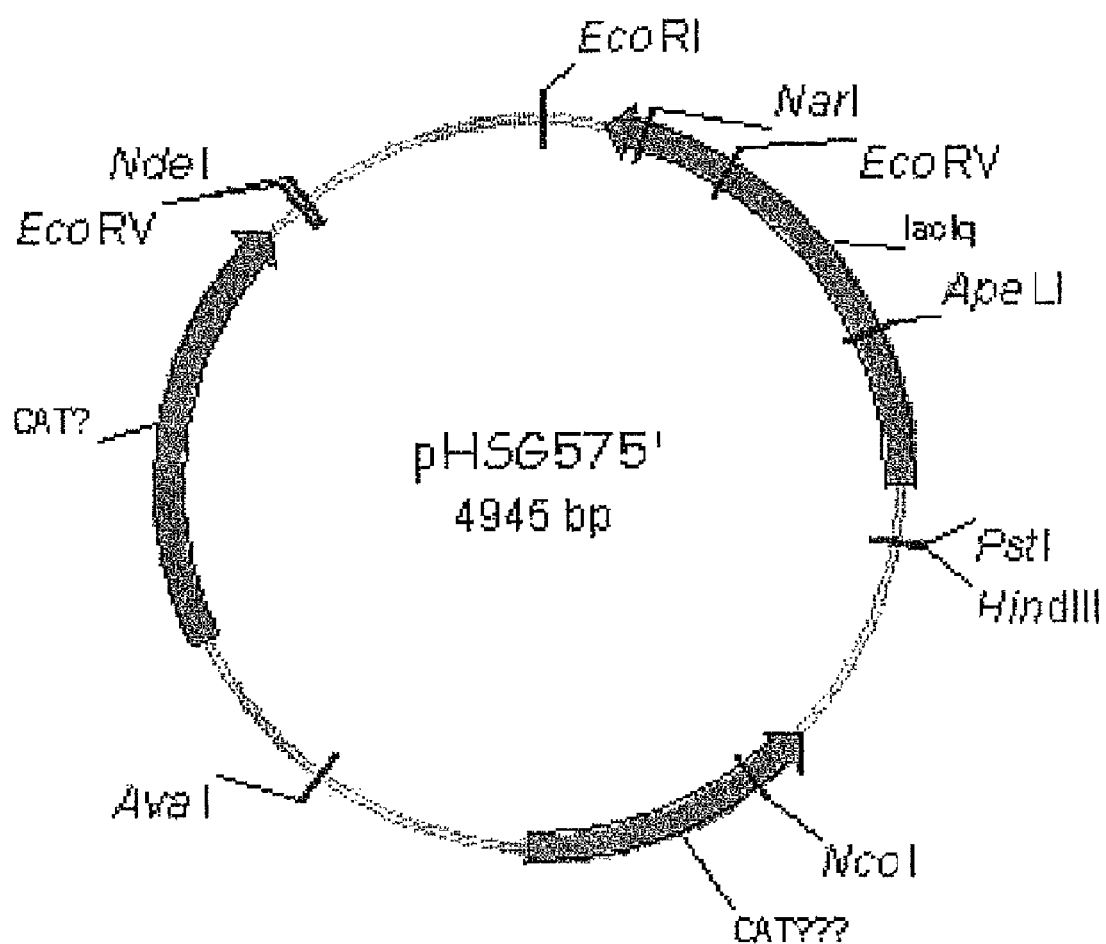
FIG. 4 the plasmid map of pHSG575'.

The recombinant *Escherichia coli* strain TG10$^+$ (OYE) was constructed as follows:

*E. coli* TG10 is derived from *E. coli* TG1 (Stratagene). TG10 is a tetracycline-resistant and rhamnose-auxotrophic strain. TG10$^+$ is derived from TG10 by introducing the following plasmids:
a) pAgro4 (chaperone+streptomycin resistance) (cf. FIG. 3) and
b) pHSG575 (chaperone+chloramphenicol resistance) (cf. FIG. 4).

pAgro4 is a derivative of the pZ vectors with groELS chaperonin genes from *E. coli*. PZ in turn is a derivative of the pACYC plasmid. pAgro4 is described for example in Nucleic Acids Res., 1997, 25, 1203, Mol. Microbiol., 2001, 40, 397.

pHSG575 is a derivative of pSC101 with lacIq repressor gene from *E. coli* and is described for example in Gene, 1987, 61, 63, Mol. Microbiol., 2001, 40, 397

TG10$^+$ (OYE) was derived from TG10$^+$ by introducing a further plasmid:
pDHE 1650 (slow rhamnose promoter+ampicillin resistance+one oye gene).

pDHE1650 is a derivative of pJOE2702 in which genes for the "old yellow enzymes" have been cloned between the NdeI and PstI or HindIII cleavage sites of pJOE2702. pJOE2702 in turn was prepared by amplifying the rhaB sequence from *E. coli* JM109 and cloning into the SphI or EcoRI cleavage sites of the pBR322 derivative pBTAC1. The ribosome binding site of pET11a and an NdeI cleavage site were obtained using synthetic oligonucleotides and placed between the BamHI/EcoRI cleavage sites of pBTAC1. The plasmid is described for example in Methods Enzymol., 1992, 216, 457, Mol. Microbiol., 1996, 21,1037.

The literature cited above is incorporated herein by reference.

The following old yellow enzymes (oye) genes were cloned:
a) oye 1: *Saccaromyces carlsbergensis* (Genbank Q02899)
b) oye 2: *Saccaromyces cerevisiae* (Genbank Q03558)
c) oye 3: *Saccaromyces cerevisiae* (Genbank P41816).

Figure 5:
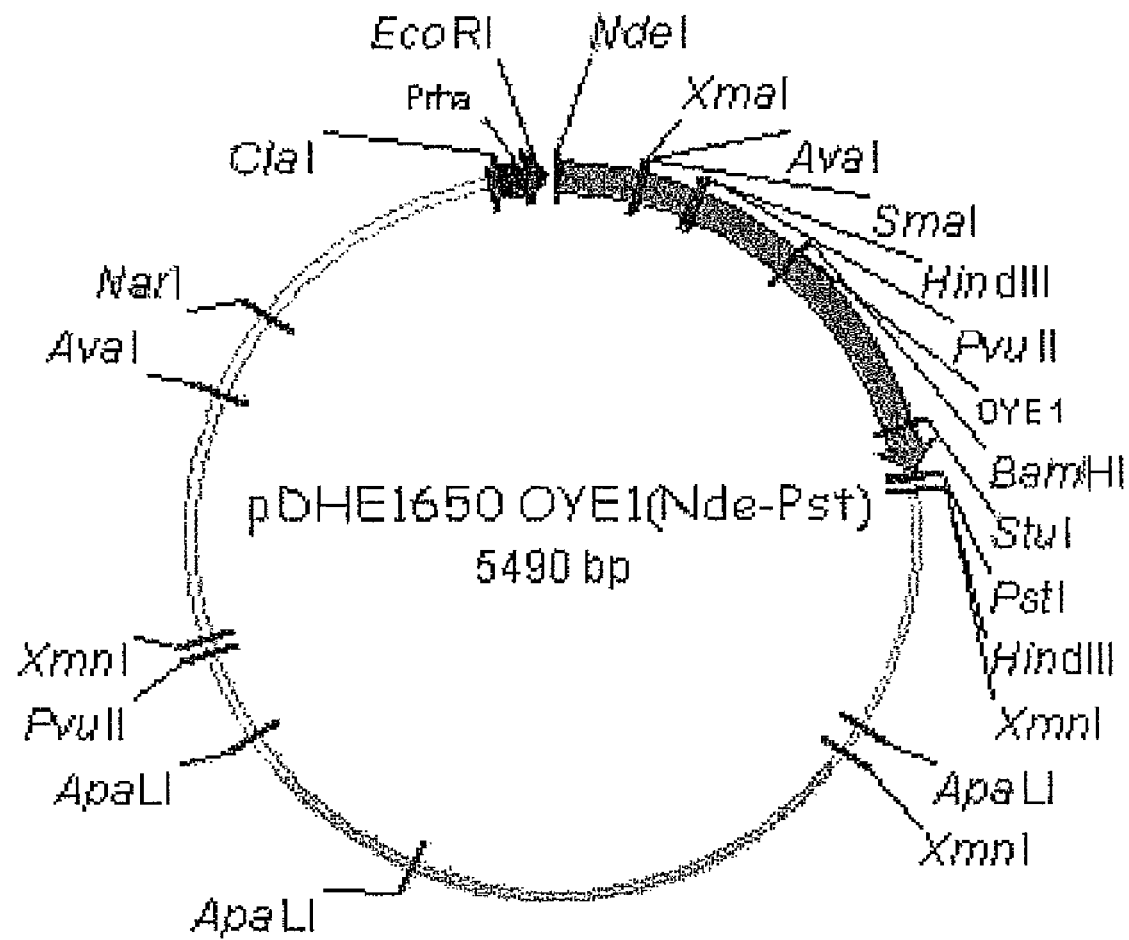
FIG. 5 the plasmid map of pDHE1658 OYE1.
Figure 6:
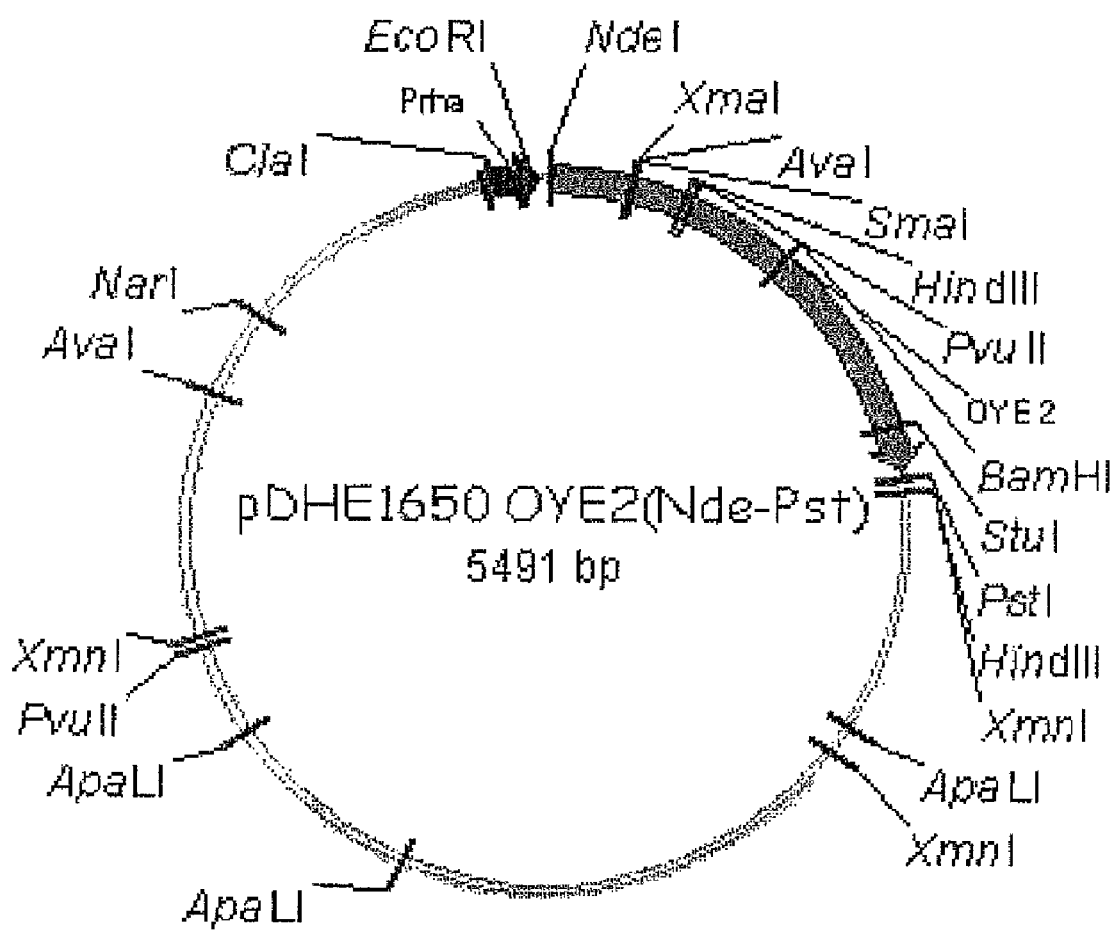
FIG. 6 the plasmid map of pDHE1658 OYE2.
Figure 7:
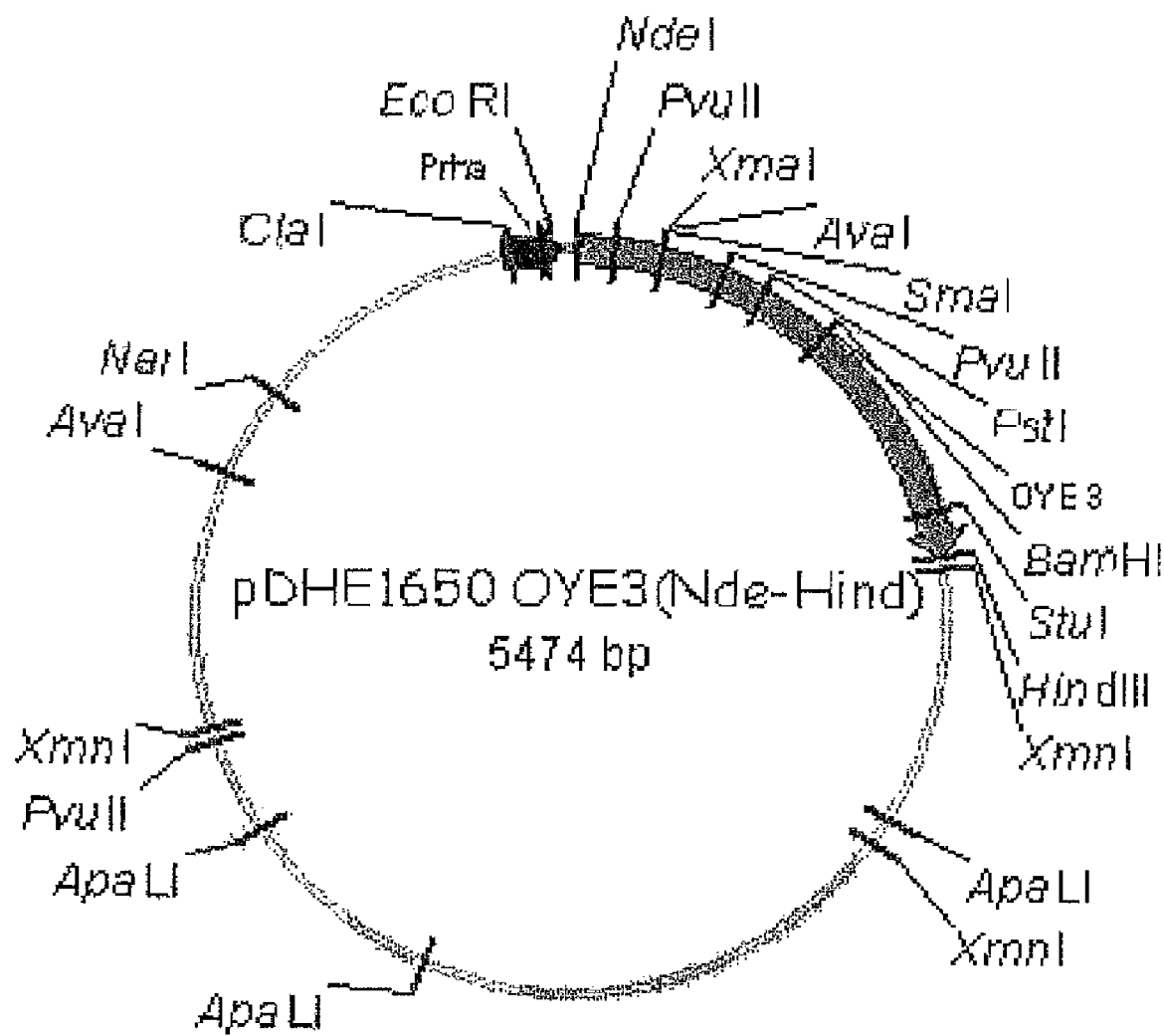
FIG. 7 the plasmid map of pDHE1658 OYE3.

The following plasmids were obtained thereby:
pDHE1650 OYE1 (cf. FIG. 5)
pDHE1650 OYE2 (cf. FIG. 6)
pDHE1650 OYE3 (cf. FIG. 7)

EXAMPLE 2

Biotransformation Experiments a) Enzyme Production

The recombinant strains were cultured in Luria broth medium (10 g/l tryptone, 10 g/l NaCl and 5 g/l yeast extract) comprising 100 µg/ml ampicillin, 100 µg/ml streptomycin and 20 µg/ml chloramphenicol. The protein overexpression was induced with 0.1 mM IPTG for both chaperones and 0.5 g/l L-rhamnose for OYE. The cultures were shaken at 120 rpm and 37° C. for 22 hours. The harvested cells were stored at −20° C.

a) Biotransformation

The biotransformations were carried out in a reaction volume of 1 ml with magnetic stirring at 30° C. over a period of 1 hour. The initial concentrations in the reaction mixture were as follows: 10 g of dry biomass/l, 10% isopropanol [volume/volume], 20 mM 4-phenyl-3-butyn-2-one, 5 mM EDTA, 2 mM NADP$^+$, 1 U/ml glucose dehydrogenase from *Thermoplasma acidophilum*, 50 mM D-glucose, 50 mM MES buffer adjusted to pH 6.8 with KOH. For biotransformations with NADH, the NADPH regeneration system (NADP$^+$, glucose dehydrogenase and glucose) was replaced by 15 mM NADH.

b) Evaluation of the Experiments

The reaction mixtures were extracted with chloroform, and the extracts were detected by capillary gas chromatography (GC) using a Varian Star 3400 GC with a Supelco BPX5 capillary column (25 m×0.32 mm internal diameter with a film thickness of the stationary phase of 0.5 µm) and FID detection. The identity of the products was confirmed by co-elution with sample standards and by GC/MS data. The GC/MS was carried out on a Hewlett-Packard 5890, series II, gas chromatograph connected to a Hewlett-Packard 5972 TID mass spectrometer using a Restek RTX-5MS capillary column (30 m×0.25 mm internal diameter with a film thickness of the stationary phase of 0.25 µm). Chromatograms and the m/z ratios were analyzed using the MSD ChemStation software from Agilent Technologies. In addition, databases were screened with the fragmentation patterns using the Wiley6 Library to identify unknown compounds. A Bruker 300 MHz GYRO NMR was used to determine the cis and trans configuration of the 4-phenyl-3-buten-2-one product formed. ID-WINNMR software was used for analysis of the data, and the resulting spectra were compared with a trans-4-phenyl-3-buten-2-one standard with a purity of 99%.

The experimental results found, expressed via the initial productivity (mM/h), are summarized in appended FIG. 1. A surprisingly specific formation of E-4-phenyl-3-buten-2-one is observed.

We claim:

1. A method for the enzymatic preparation of an alkenone of formula (2) from an α,β-unsaturated alkynone of formula (1)

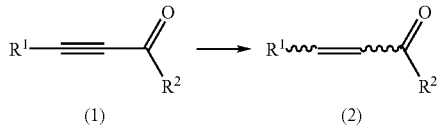

wherein
R$^1$ is H, C$_1$-C$_6$-alkyl, C$_2$-C$_6$-alkenyl, or an optionally substituted carbo- or heterocyclic aromatic or nonaromatic ring; and
R$^2$ is H, C$_1$-C$_6$-alkyl, or C$_2$-C$_6$-alkenyl;
comprising reducing the compound of formula (1) in the presence of:
(i) a reductase comprising at least one polypeptide selected from the group consiting of SEQ ID NO: 1, 2, 3, 5, 7, and 9; or
(ii) with a functionally equivalent reductase which has at least 80% sequence identity with SEQ ID NO: 1, 2, 3, 5, 7, and 9;
wherein
the reaction is carred out:
(i) in an essentially ATP-free environment, wherein the reductase or functionally equivalent reductase is in the form of (a) a purified reductase, (b) an enriched reductase, or (c) a protein fraction comprising the reductase; or
(ii) with a reconbinant bacterial microorganism that expresses the reductase or functionally equivalent reductase; and
the reaction is carried out with NADPH or NADH as cofactor.

2. The method of claim 1, wherein said cofactor is regenerated enzymatically.

3. The method of claim 2, wherein said cofactor is regenerated by glucose dehydrogenase.

4. The method of claim 1, wherein the reduction takes place in an aqueous, aqueous-alcoholic, or alcoholic reaction medium.

5. The method of claim 1, wherein the reductase or functionally equivalent reductase is in immobilized form.

6. The method of claim 1, wherein said reductase is selected from the group consisting of SEQ ID Nos. 1, 2 and 3.

7. The method of claim 1, wherein R$^1$ is optionally substituted aryl and R$^2$ is C$_1$-C$_6$-alkyl.

8. The method of claim 1, wherein an E isomer of compound of formula (2) is obtained.

9. The method of claim 1, wherein the reaction takes place at a temperature from 0 to 45° C. and/or at a pH from 6 to 8.

* * * * *

SEQUENCE LISTING

<160> NUMBER OF SEQ ID NOS: 9

<210> SEQ ID NO 1
<211> LENGTH: 399
<212> TYPE: PRT
<213> ORGANISM: Saccharomyces carlsbergensis

<400> SEQUENCE: 1

Ser Phe Val Lys Asp Phe Lys Pro Gln Ala Leu Gly Asp Thr Asn Leu
1               5                   10                  15

Phe Lys Pro Ile Lys Ile Gly Asn Asn Glu Leu Leu His Arg Ala Val
            20                  25                  30

Ile Pro Pro Leu Thr Arg Met Arg Ala Leu His Pro Gly Asn Ile Pro
            35                  40                  45

Asn Arg Asp Trp Ala Val Glu Tyr Tyr Thr Gln Arg Ala Gln Arg Pro
 50                  55                  60

Gly Thr Met Ile Ile Thr Glu Gly Ala Phe Ile Ser Pro Gln Ala Gly
 65                  70                  75                  80

Gly Tyr Asp Asn Ala Pro Gly Val Trp Ser Glu Glu Gln Met Val Glu
                 85                  90                  95

Trp Thr Lys Ile Phe Asn Ala Ile His Glu Lys Lys Ser Phe Val Trp
            100                 105                 110

Val Gln Leu Trp Val Leu Gly Trp Ala Ala Phe Pro Asp Asn Leu Ala
            115                 120                 125

Arg Asp Gly Leu Arg Tyr Asp Ser Ala Ser Asp Asn Val Phe Met Asp
 130                 135                 140

Ala Glu Gln Glu Ala Lys Ala Lys Lys Ala Asn Asn Pro Gln His Ser
145                 150                 155                 160

Leu Thr Lys Asp Glu Ile Lys Gln Tyr Ile Lys Glu Tyr Val Gln Ala
                165                 170                 175

Ala Lys Asn Ser Ile Ala Ala Gly Ala Asp Gly Val Glu Ile His Ser
            180                 185                 190

Ala Asn Gly Tyr Leu Leu Asn Gln Phe Leu Asp Pro His Ser Asn Thr
            195                 200                 205

Arg Thr Asp Glu Tyr Gly Gly Ser Ile Glu Asn Arg Ala Arg Phe Thr
 210                 215                 220

Leu Glu Val Val Asp Ala Leu Val Glu Ala Ile Gly His Glu Lys Val
225                 230                 235                 240

Gly Leu Arg Leu Ser Pro Tyr Gly Val Phe Asn Ser Met Ser Gly Gly
                245                 250                 255

Ala Glu Thr Gly Ile Val Ala Gln Tyr Ala Tyr Val Ala Gly Glu Leu
            260                 265                 270

Glu Lys Arg Ala Lys Ala Gly Lys Arg Leu Ala Phe Val His Leu Val
            275                 280                 285

Glu Pro Arg Val Thr Asn Pro Phe Leu Thr Glu Gly Glu Gly Glu Tyr
 290                 295                 300

Glu Gly Gly Ser Asn Asp Phe Val Tyr Ser Ile Trp Lys Gly Pro Val
305                 310                 315                 320

Ile Arg Ala Gly Asn Phe Ala Leu His Pro Glu Val Val Arg Glu Glu
                325                 330                 335

Val Lys Asp Lys Arg Thr Leu Ile Gly Tyr Gly Arg Phe Phe Ile Ser
            340                 345                 350

Asn Pro Asp Leu Val Asp Arg Leu Glu Lys Gly Leu Pro Leu Asn Lys
            355                 360                 365

Tyr Asp Arg Asp Thr Phe Tyr Gln Met Ser Ala His Gly Tyr Ile Asp
 370                 375                 380

Tyr Pro Thr Tyr Glu Glu Ala Leu Lys Leu Gly Trp Asp Lys Lys
385                 390                 395

<210> SEQ ID NO 2
<211> LENGTH: 399
<212> TYPE: PRT
<213> ORGANISM: Saccharomyces cerevisiae

<400> SEQUENCE: 2

Pro Phe Val Lys Asp Phe Lys Pro Gln Ala Leu Gly Asp Thr Asn Leu
 1               5                  10                  15

```
Phe Lys Pro Ile Lys Ile Gly Asn Asn Glu Leu Leu His Arg Ala Val
             20                  25                  30
Ile Pro Pro Leu Thr Arg Met Arg Ala Gln His Pro Gly Asn Ile Pro
         35                  40                  45
Asn Arg Asp Trp Ala Val Glu Tyr Tyr Ala Gln Arg Ala Gln Arg Pro
     50                  55                  60
Gly Thr Leu Ile Ile Thr Glu Gly Thr Phe Pro Ser Pro Gln Ser Gly
 65                  70                  75                  80
Gly Tyr Asp Asn Ala Pro Gly Ile Trp Ser Glu Glu Gln Ile Lys Glu
                 85                  90                  95
Trp Thr Lys Ile Phe Lys Ala Ile His Glu Asn Lys Ser Phe Ala Trp
            100                 105                 110
Val Gln Leu Trp Val Leu Gly Trp Ala Ala Phe Pro Asp Thr Leu Ala
        115                 120                 125
Arg Asp Gly Leu Arg Tyr Asp Ser Ala Ser Asp Asn Val Tyr Met Asn
    130                 135                 140
Ala Glu Gln Glu Glu Lys Ala Lys Lys Ala Asn Asn Pro Gln His Ser
145                 150                 155                 160
Ile Thr Lys Asp Glu Ile Lys Gln Tyr Val Lys Glu Tyr Val Gln Ala
                165                 170                 175
Ala Lys Asn Ser Ile Ala Ala Gly Ala Asp Gly Val Glu Ile His Ser
            180                 185                 190
Ala Asn Gly Tyr Leu Leu Asn Gln Phe Leu Asp Pro His Ser Asn Asn
        195                 200                 205
Arg Thr Asp Glu Tyr Gly Gly Ser Ile Glu Asn Arg Ala Arg Phe Thr
    210                 215                 220
Leu Glu Val Val Asp Ala Val Asp Ala Ile Gly Pro Glu Lys Val
225                 230                 235                 240
Gly Leu Arg Leu Ser Pro Tyr Gly Val Phe Asn Ser Met Ser Gly Gly
                245                 250                 255
Ala Glu Thr Gly Ile Val Ala Gln Tyr Ala Tyr Val Leu Gly Glu Leu
            260                 265                 270
Glu Arg Arg Ala Lys Ala Gly Lys Arg Leu Ala Phe Val His Leu Val
        275                 280                 285
Glu Pro Arg Val Thr Asn Pro Phe Leu Thr Gly Glu Gly Glu Tyr
    290                 295                 300
Asn Gly Gly Ser Asn Lys Phe Ala Tyr Ser Ile Trp Lys Gly Pro Ile
305                 310                 315                 320
Ile Arg Ala Gly Asn Phe Ala Leu His Pro Glu Val Val Arg Glu Glu
                325                 330                 335
Val Lys Asp Pro Arg Thr Leu Ile Gly Tyr Gly Arg Phe Phe Ile Ser
            340                 345                 350
Asn Pro Asp Leu Val Asp Arg Leu Glu Lys Gly Leu Pro Leu Asn Lys
        355                 360                 365
Tyr Asp Arg Asp Thr Phe Tyr Lys Met Ser Ala Glu Gly Tyr Ile Asp
    370                 375                 380
Tyr Pro Thr Tyr Glu Glu Ala Leu Lys Leu Gly Trp Asp Lys Asn
385                 390                 395
```

<210> SEQ ID NO 3
<211> LENGTH: 399
<212> TYPE: PRT
<213> ORGANISM: Saccharomyces cerevisiae

<400> SEQUENCE: 3

```
Pro Phe Val Lys Gly Phe Glu Pro Ile Ser Leu Arg Asp Thr Asn Leu
1               5                   10                  15

Phe Glu Pro Ile Lys Ile Gly Asn Thr Gln Leu Ala His Arg Ala Val
            20                  25                  30

Met Pro Pro Leu Thr Arg Met Arg Ala Thr His Pro Gly Asn Ile Pro
        35                  40                  45

Asn Lys Glu Trp Ala Ala Val Tyr Tyr Gly Gln Arg Ala Gln Arg Pro
    50                  55                  60

Gly Thr Met Ile Ile Thr Glu Gly Thr Phe Ile Ser Pro Gln Ala Gly
65                      70                  75                  80

Gly Tyr Asp Asn Ala Pro Gly Ile Trp Ser Asp Glu Gln Val Ala Glu
                85                  90                  95

Trp Lys Asn Ile Phe Leu Ala Ile His Asp Cys Gln Ser Phe Ala Trp
                100                 105                 110

Val Gln Leu Trp Ser Leu Gly Trp Ala Ser Phe Pro Asp Val Leu Ala
            115                 120                 125

Arg Asp Gly Leu Arg Tyr Asp Cys Ala Ser Asp Arg Val Tyr Met Asn
        130                 135                 140

Ala Thr Leu Gln Glu Lys Ala Lys Asp Ala Asn Asn Leu Glu His Ser
145                 150                 155                 160

Leu Thr Lys Asp Asp Ile Lys Gln Tyr Ile Lys Asp Tyr Ile His Ala
                165                 170                 175

Ala Lys Asn Ser Ile Ala Ala Gly Ala Asp Gly Val Glu Ile His Ser
                180                 185                 190

Ala Asn Gly Tyr Leu Leu Asn Gln Phe Leu Asp Pro His Ser Asn Lys
            195                 200                 205

Arg Thr Asp Glu Tyr Gly Gly Thr Ile Glu Asn Arg Ala Arg Phe Thr
        210                 215                 220

Leu Glu Val Val Asp Ala Leu Ile Glu Thr Ile Gly Pro Glu Arg Val
225                 230                 235                 240

Gly Leu Arg Leu Ser Pro Tyr Gly Thr Phe Asn Ser Met Ser Gly Gly
                245                 250                 255

Ala Glu Pro Gly Ile Ile Ala Gln Tyr Ser Tyr Val Leu Gly Glu Leu
            260                 265                 270

Glu Lys Arg Ala Lys Ala Gly Lys Arg Leu Ala Phe Val His Leu Val
        275                 280                 285

Glu Pro Arg Val Thr Asp Pro Ser Leu Val Glu Gly Glu Gly Glu Tyr
    290                 295                 300

Ser Glu Gly Thr Asn Asp Phe Ala Tyr Ser Ile Trp Lys Gly Pro Ile
305                 310                 315                 320

Ile Arg Ala Gly Asn Tyr Ala Leu His Pro Glu Val Val Arg Glu Gln
                325                 330                 335

Val Lys Asp Pro Arg Thr Leu Ile Gly Tyr Gly Arg Phe Phe Ile Ser
            340                 345                 350

Asn Pro Asp Leu Val Tyr Arg Leu Glu Glu Gly Leu Pro Leu Asn Lys
        355                 360                 365

Tyr Asp Arg Ser Thr Phe Tyr Thr Met Ser Ala Glu Gly Tyr Thr Asp
370                 375                 380

Tyr Pro Thr Tyr Glu Glu Ala Val Asp Leu Gly Trp Asn Lys Asn
385                 390                 395
```

<210> SEQ ID NO 4
<211> LENGTH: 5490
<212> TYPE: DNA

```
<213> ORGANISM: Artificial
<220> FEATURE:
<223> OTHER INFORMATION: Plamid encoding OYE1
<220> FEATURE:
<221> NAME/KEY: CDS
<222> LOCATION: (4)..(1203)

<400> SEQUENCE: 4
```

| | | | | | | | | | | | | | | | | |
|---|---|---|---|---|---|---|---|---|---|---|---|---|---|---|---|---|
| cat | atg | agc | ttt | gtg | aaa | gat | ttt | aaa | ccg | cag | gcg | ctg | ggc | gat | acc | 48 |
| | Met | Ser | Phe | Val | Lys | Asp | Phe | Lys | Pro | Gln | Ala | Leu | Gly | Asp | Thr | |
| | 1 | | | 5 | | | | | 10 | | | | | | 15 | |

| aac | ctg | ttt | aaa | ccg | att | aaa | att | ggc | aac | aac | gaa | ctg | ctg | cat | cgc | 96 |
|---|---|---|---|---|---|---|---|---|---|---|---|---|---|---|---|---|
| Asn | Leu | Phe | Lys | Pro | Ile | Lys | Ile | Gly | Asn | Asn | Glu | Leu | Leu | His | Arg | |
| | | | 20 | | | | 25 | | | | | 30 | | | | |

| gcg | gtg | att | ccg | ccg | ctg | acc | cgc | atg | cgc | gcg | ctg | cat | ccg | ggc | aac | 144 |
|---|---|---|---|---|---|---|---|---|---|---|---|---|---|---|---|---|
| Ala | Val | Ile | Pro | Pro | Leu | Thr | Arg | Met | Arg | Ala | Leu | His | Pro | Gly | Asn | |
| | | 35 | | | | 40 | | | | | 45 | | | | | |

| att | ccg | aac | cgc | gat | tgg | gcg | gtg | gaa | tat | tat | acc | cag | cgc | gcg | cag | 192 |
|---|---|---|---|---|---|---|---|---|---|---|---|---|---|---|---|---|
| Ile | Pro | Asn | Arg | Asp | Trp | Ala | Val | Glu | Tyr | Tyr | Thr | Gln | Arg | Ala | Gln | |
| | 50 | | | | 55 | | | | | 60 | | | | | | |

| cgc | ccg | ggc | acc | atg | att | att | acc | gaa | ggc | gcg | ttt | att | agc | ccg | cag | 240 |
|---|---|---|---|---|---|---|---|---|---|---|---|---|---|---|---|---|
| Arg | Pro | Gly | Thr | Met | Ile | Ile | Thr | Glu | Gly | Ala | Phe | Ile | Ser | Pro | Gln | |
| 65 | | | | 70 | | | | | 75 | | | | | | | |

| gcg | ggc | ggc | tat | gat | aac | gcg | ccg | ggc | gtg | tgg | agc | gaa | gaa | cag | atg | 288 |
|---|---|---|---|---|---|---|---|---|---|---|---|---|---|---|---|---|
| Ala | Gly | Gly | Tyr | Asp | Asn | Ala | Pro | Gly | Val | Trp | Ser | Glu | Glu | Gln | Met | |
| 80 | | | | 85 | | | | | 90 | | | | | 95 | | |

| gtg | gaa | tgg | acc | aaa | att | ttt | aac | gcg | att | cat | gaa | aaa | aaa | agc | ttt | 336 |
|---|---|---|---|---|---|---|---|---|---|---|---|---|---|---|---|---|
| Val | Glu | Trp | Thr | Lys | Ile | Phe | Asn | Ala | Ile | His | Glu | Lys | Lys | Ser | Phe | |
| | | | 100 | | | | | 105 | | | | | 110 | | | |

| gtg | tgg | gtg | cag | ctg | tgg | gtg | ctg | ggc | tgg | gcg | gcg | ttt | ccg | gat | aac | 384 |
|---|---|---|---|---|---|---|---|---|---|---|---|---|---|---|---|---|
| Val | Trp | Val | Gln | Leu | Trp | Val | Leu | Gly | Trp | Ala | Ala | Phe | Pro | Asp | Asn | |
| | | 115 | | | | | 120 | | | | | 125 | | | | |

| ctg | gcg | cgc | gat | ggc | ctg | cgc | tat | gat | agc | gcg | agc | gat | aac | gtg | ttt | 432 |
|---|---|---|---|---|---|---|---|---|---|---|---|---|---|---|---|---|
| Leu | Ala | Arg | Asp | Gly | Leu | Arg | Tyr | Asp | Ser | Ala | Ser | Asp | Asn | Val | Phe | |
| | | 130 | | | | | 135 | | | | | 140 | | | | |

| atg | gat | gcg | gaa | cag | gaa | gcg | aaa | gcg | aaa | aaa | gcg | aac | aac | ccg | cag | 480 |
|---|---|---|---|---|---|---|---|---|---|---|---|---|---|---|---|---|
| Met | Asp | Ala | Glu | Gln | Glu | Ala | Lys | Ala | Lys | Lys | Ala | Asn | Asn | Pro | Gln | |
| 145 | | | | | 150 | | | | | 155 | | | | | | |

| cat | agc | ctg | acc | aaa | gat | gaa | att | aaa | cag | tat | att | aaa | gaa | tat | gtg | 528 |
|---|---|---|---|---|---|---|---|---|---|---|---|---|---|---|---|---|
| His | Ser | Leu | Thr | Lys | Asp | Glu | Ile | Lys | Gln | Tyr | Ile | Lys | Glu | Tyr | Val | |
| 160 | | | | 165 | | | | | 170 | | | | | 175 | | |

| cag | gcg | gcg | aaa | aac | agc | att | gcg | gcg | ggc | gcg | gat | ggc | gtg | gaa | att | 576 |
|---|---|---|---|---|---|---|---|---|---|---|---|---|---|---|---|---|
| Gln | Ala | Ala | Lys | Asn | Ser | Ile | Ala | Ala | Gly | Ala | Asp | Gly | Val | Glu | Ile | |
| | | | 180 | | | | | 185 | | | | | 190 | | | |

| cat | agc | gcg | aac | ggc | tat | ctg | ctg | aac | cag | ttt | ctg | gat | ccg | cat | agc | 624 |
|---|---|---|---|---|---|---|---|---|---|---|---|---|---|---|---|---|
| His | Ser | Ala | Asn | Gly | Tyr | Leu | Leu | Asn | Gln | Phe | Leu | Asp | Pro | His | Ser | |
| | | 195 | | | | | 200 | | | | | 205 | | | | |

| aac | acc | cgc | acc | gat | gaa | tat | ggc | ggc | agc | att | gaa | aac | cgc | gcg | cgc | 672 |
|---|---|---|---|---|---|---|---|---|---|---|---|---|---|---|---|---|
| Asn | Thr | Arg | Thr | Asp | Glu | Tyr | Gly | Gly | Ser | Ile | Glu | Asn | Arg | Ala | Arg | |
| | 210 | | | | | 215 | | | | | 220 | | | | | |

| ttt | acc | ctg | gaa | gtg | gtg | gat | gcg | ctg | gtg | gaa | gcg | att | ggc | cat | gaa | 720 |
|---|---|---|---|---|---|---|---|---|---|---|---|---|---|---|---|---|
| Phe | Thr | Leu | Glu | Val | Val | Asp | Ala | Leu | Val | Glu | Ala | Ile | Gly | His | Glu | |
| 225 | | | | | 230 | | | | | 235 | | | | | | |

| aaa | gtg | ggc | ctg | cgc | ctg | agc | ccg | tat | ggc | gtg | ttt | aac | agc | atg | agc | 768 |
|---|---|---|---|---|---|---|---|---|---|---|---|---|---|---|---|---|
| Lys | Val | Gly | Leu | Arg | Leu | Ser | Pro | Tyr | Gly | Val | Phe | Asn | Ser | Met | Ser | |
| 240 | | | | 245 | | | | | 250 | | | | | 255 | | |

| ggc | ggc | gcg | gaa | acc | ggc | att | gtg | gcg | cag | tat | gcg | tat | gtg | gcg | ggc | 816 |
|---|---|---|---|---|---|---|---|---|---|---|---|---|---|---|---|---|
| Gly | Gly | Ala | Glu | Thr | Gly | Ile | Val | Ala | Gln | Tyr | Ala | Tyr | Val | Ala | Gly | |
| | | | 260 | | | | | 265 | | | | | 270 | | | |

| gaa | ctg | gaa | aaa | cgc | gcg | aaa | gcg | ggc | aaa | cgc | ctg | gcg | ttt | gtg | cat | 864 |
|---|---|---|---|---|---|---|---|---|---|---|---|---|---|---|---|---|
| Glu | Leu | Glu | Lys | Arg | Ala | Lys | Ala | Gly | Lys | Arg | Leu | Ala | Phe | Val | His | |
| | | 275 | | | | | 280 | | | | | 285 | | | | |

```
ctg gtg gaa ccg cgc gtg acc aac ccg ttt ctg acc gaa ggc gaa ggc      912
Leu Val Glu Pro Arg Val Thr Asn Pro Phe Leu Thr Glu Gly Glu Gly
        290                 295                 300 gaa tat gaa ggc ggc agc aac gat ttt gtg tat agc att tgg aaa ggc      960
Glu Tyr Glu Gly Gly Ser Asn Asp Phe Val Tyr Ser Ile Trp Lys Gly
    305                 310                 315 ccg gtg att cgc gcg ggc aac ttt gcg ctg cat ccg gaa gtg gtg cgc     1008
Pro Val Ile Arg Ala Gly Asn Phe Ala Leu His Pro Glu Val Val Arg
320                 325                 330                 335 gaa gaa gtg aaa gat aaa cgc acc ctg att ggc tat ggc cgc ttt ttt     1056
Glu Glu Val Lys Asp Lys Arg Thr Leu Ile Gly Tyr Gly Arg Phe Phe
                340                 345                 350 att agc aac ccg gat ctg gtg gat cgc ctg gaa aaa ggc ctg ccg ctg     1104
Ile Ser Asn Pro Asp Leu Val Asp Arg Leu Glu Lys Gly Leu Pro Leu
            355                 360                 365 aac aaa tat gat cgc gat acc ttt tat cag atg agc gcg cat ggc tat     1152
Asn Lys Tyr Asp Arg Asp Thr Phe Tyr Gln Met Ser Ala His Gly Tyr
        370                 375                 380 att gat tat ccg acc tat gaa gaa gcg ctg aaa ctg ggc tgg gat aaa     1200
Ile Asp Tyr Pro Thr Tyr Glu Glu Ala Leu Lys Leu Gly Trp Asp Lys
    385                 390                 395 aaa tgacttaact gcagccaagc ttggctgttt tggcggatga gagaagattt          1253
Lys
400 tcagcctgat acagattaaa tcagaacgca gaagcggtct gataaaacag aatttgcctg   1313 gcggcagtag cgcggtggtc ccacctgacc ccatgccgaa ctcagaagtg aaacgccgta   1373 gcgccgatgg tagtgtgggg tctccccatg cgagagtagg gaactgccag gcatcaaata   1433 aaacgaaagg ctcagtcgaa agactgggcc tttcgtttta tctgttgttt gtcggtgaac   1493 gctctcctga gtaggacaaa tccgccggga gcggatttga acgttgcgaa gcaacggccc   1553 ggagggtggc gggcaggacg cccgccataa actgccaggc atcaaattaa gcagaaggcc   1613 atcctgacgg atggcctttt tgcgtttcta caaactcttt tgtttatttt tctaaataca   1673 ttcaaatatg tatccgctca tgagacaata accctgataa atgcttcaat aatattgaaa   1733 aggaagagta tgagtattca acatttccgt gtcgccctta ttccctttttt gcggcattt   1793 tgccttcctg ttttgctca cccagaaacg ctggtgaaag taaaagatgc tgaagatcag   1853 ttgggtgcac gagtgggtta catcgaactg gatctcaaca gcggtaagat ccttgagagt   1913 tttcgccccg aagaacgttt tccaatgatg agcacttttta aagttctgct atgtggcgcg   1973 gtattatccc gtgttgacgc cgggcaagag caactcggtc gccgcataca ctattctcag   2033 aatgacttgg ttgagtactc accagtcaca gaaaagcatc ttacggatgg catgacagta   2093 agagaattat gcagtgctgc cataaccatg agtgataaca ctgcggccaa cttacttctg   2153 acaacgatcg gaggaccgaa ggagctaacc gcttttttgc acaacatggg gatcatgta   2213 actcgccttg atcgttggga accggagctg aatgaagcca taccaaacga cgagcgtgac   2273 accacgatgc ctgtagcaat ggcaacaacg ttgcgcaaac tattaactgg cgaactactt   2333 actctagctt cccggcaaca attaatagac tggatggagg cggataaagt tgcaggacca   2393 cttctgcgct cggcccttcc ggctggctgg tttattgctg ataaatctgg agccggtgag   2453 cgtgggtctc gcggtatcat tgcagcactg gggccagatg gtaagccctc ccgtatcgta   2513 gttatctaca cgacggggag tcaggcaact atggatgaac gaaatagaca gatcgctgag   2573 ataggtgcct cactgattaa gcattggtaa ctgtcagacc aagtttactc atatatactt   2633 tagattgatt taaaacttca tttttaattt aaaaggatct aggtgaagat cctttttgat   2693
```

```
aatctcatga ccaaaatccc ttaacgtgag ttttcgttcc actgagcgtc agacccgta    2753 gaaaagatca aaggatcttc ttgagatcct ttttttctgc gcgtaatctg ctgcttgcaa   2813
acaaaaaaac caccgctacc agcggtggtt tgtttgccgg atcaagagct accaactctt   2873
tttccgaagg taactggctt cagcagagcg cagataccaa atactgtcct tctagtgtag   2933
ccgtagttag gccaccactt caagaactct gtagcaccgc ctacatacct cgctctgcta   2993
atcctgttac cagtggctgc tgccagtggc gataagtcgt gtcttaccgg gttggactca   3053
agacgatagt taccggataa ggcgcagcgg tcgggctgaa cggggggttc gtgcacacag   3113
cccagcttgg agcgaacgac ctacaccgaa ctgagatacc tacagcgtga gctatgagaa   3173
agcgccacgc ttcccgaagg gagaaaggcg gacaggtatc cggtaagcgg cagggtcgga   3233
acaggagagc gcacgaggga gcttccaggg ggaaacgcct ggtatcttta tagtcctgtc   3293
gggtttcgcc acctctgact tgagcgtcga ttttgtgat gctcgtcagg ggggcggagc    3353
ctatggaaaa acgccagcaa cgcggccttt ttacggttcc tggccttttg ctggccttt    3413 gctcacatgt tctttcctgc gttatcccct gattctgtgg ataaccgtat taccgccttt   3473
gagtgagctg ataccgctcg ccgcagccga acgaccgagc gcagcgagtc agtgagcgag   3533
gaagcggaag agcgcctgat gcggtatttt ctccttacgc atctgtgcgg tatttcacac   3593
cgcatatatg gtgcactctc agtacaatct gctctgatgc cgcatagtta agccagtata   3653
cactccgcta tcgctacgtg actgggtcat ggctgcgccc cgacacccgc caacacccgc   3713
tgacgcgccc tgacgggctt gtctgctccc ggcatccgct tacagacaag ctgtgaccgt   3773
ctccgggagc tgcatgtgtc agaggttttc accgtcatca ccgaaacgcg cgaggcagct   3833
gcggtaaagc tcatcagcgt ggtcgtgaag cgattcacag atgtctgcct gttcatccgc   3893
gtccagctcg ttgagtttct ccagaagcgt taatgtctgg cttctgataa agcgggccat   3953
gttaagggcg gttttttcct gtttggtcac ttgatgcctc cgtgtaaggg ggaatttctg   4013
ttcatggggg taatgatacc gatgaaacga gagaggatgc tcacgatacg ggttactgat   4073
gatgaacatg cccggttact ggaacgttgt gagggtaaac aactggcggt atggatgcgg   4133
cgggaccaga gaaaaatcac tcagggtcaa tgccagcgct tcgttaatac agatgtaggt   4193
gttccacagg gtagccagca gcatcctgcg atgcagatcc ggaacataat ggtgcagggc   4253
gctgacttcc gcgtttccag actttacgaa acacggaaac cgaagaccat tcatgttgtt   4313
gctcaggtcg cagacgtttt gcagcagcag tcgcttcacg ttcgctcgcg tatcggtgat   4373
tcattctgct aaccagtaag gcaaccccgc cagcctagcc gggtcctcaa cgacaggagc   4433
acgatcatgc gcacccgtgg ccaggaccca acgctgcccg agatgcgccg cgtgcggctg   4493
ctggagatgg cggacgcgat ggatatgttc tgccaagggt tggtttgcgc attcacagtt   4553
ctccgcaaga attgattggc tccaattctt ggagtggtga atccgttagc gaggtgccgc   4613
cggcttccat tcaggtcgag gtggcccggc tccatgcacc gcgacgcaac gcggggaggc   4673
agacaaggta tagggcggcg cctacaatcc atgccaaccc gttccatgtg ctcgccgagg   4733
cggcataaat cgccgtgacg atcagcggtc cagtgatcga agttaggctg gtaagagccg   4793
cgagcgatcc ttgaagctgt ccctgatggt cgtcatctac ctgcctggac agcatggcct   4853
gcaacgcggg catcccgatg ccgccggaag cgagaagaat cataatgggg aaggccatcc   4913
agcctcgcgt cgcgaacgcc agcaagacgt agcccagcgc gtcggccgcc atgccggcga   4973
taatggcctg cttctcgccg aaacgtttgg tggcgggacc agtgacgaag gcttgagcga   5033
gggcgtgcaa gattccgaat accgcaagcg acaggccgat catcgtcgcg ctccagcgaa   5093
```

```
agcggtcctc gccgaaaatg acccagagcg ctgccggcac ctgtcctacg agttgcatga   5153
taaagaagac agtcataagt gcggcgacga tagtcatgcc ccgcgcccac cggaaggagc   5213
tgactgggtt gaaggctctc aagggcatcg gtcgacgctc tcccttatgc gactcctgca   5273
ttaggaagca gcccagtagt aggttgaggc cgttgagcac cgccgccgca aggaatggtg   5333
catgcatcga tcaccacaat tcagcaaatt gtgaacatca tcacgttcat ctttccctgg   5393
ttgccaatgg cccatttttcc tgtcagtaac gagaaggtcg cgaattcagg cgcttttttag  5453 actggtcgta atgaacaatt cttaagaagg agatata                             5490
```

<210> SEQ ID NO 5
<211> LENGTH: 400
<212> TYPE: PRT
<213> ORGANISM: Artificial
<220> FEATURE:
<223> OTHER INFORMATION: Synthetic Construct

<400> SEQUENCE: 5

```
Met Ser Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
    50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Val Trp Ser Glu Glu Gln Met Val
                85                  90                  95

Glu Trp Thr Lys Ile Phe Asn Ala Ile His Glu Lys Lys Ser Phe Val
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Phe Met
    130                 135                 140

Asp Ala Glu Gln Glu Ala Lys Ala Lys Lys Ala Asn Asn Pro Gln His
145                 150                 155                 160

Ser Leu Thr Lys Asp Glu Ile Lys Gln Tyr Ile Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Thr Arg Thr Asp Glu Tyr Gly Gly Ser Ile Glu Asn Arg Ala Arg Phe
    210                 215                 220

Thr Leu Glu Val Val Asp Ala Leu Val Glu Ala Ile Gly His Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Ala Gly Glu
            260                 265                 270

Leu Glu Lys Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
```

```
              290                 295                 300
Tyr Glu Gly Gly Ser Asn Asp Phe Val Tyr Ser Ile Trp Lys Gly Pro
305                 310                 315                 320

Val Ile Arg Ala Gly Asn Phe Ala Leu His Pro Glu Val Val Arg Glu
                325                 330                 335

Glu Val Lys Asp Lys Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Gln Met Ser Ala His Gly Tyr Ile
    370                 375                 380

Asp Tyr Pro Thr Tyr Glu Glu Ala Leu Lys Leu Gly Trp Asp Lys Lys
385                 390                 395                 400

<210> SEQ ID NO 6
<211> LENGTH: 5491
<212> TYPE: DNA
<213> ORGANISM: Artificial
<220> FEATURE:
<223> OTHER INFORMATION: Plasmid encoding OYE2
<220> FEATURE:
<221> NAME/KEY: CDS
<222> LOCATION: (4)..(1203)

<400> SEQUENCE: 6 cat atg ccg ttt gtg aaa gat ttt aaa ccg cag gcg ctg ggc gat acc      48
    Met Pro Phe Val Lys Asp Phe Lys Pro Gln Ala Leu Gly Asp Thr
    1               5                   10                  15 aac ctg ttt aaa ccg att aaa att ggc aac aac gaa ctg ctg cat cgc      96
Asn Leu Phe Lys Pro Ile Lys Ile Gly Asn Asn Glu Leu Leu His Arg
            20                  25                  30 gcg gtg att ccg ccg ctg acc cgc atg cgc gcg cag cat ccg ggc aac     144
Ala Val Ile Pro Pro Leu Thr Arg Met Arg Ala Gln His Pro Gly Asn
        35                  40                  45 att ccg aac cgc gat tgg gcg gtg gaa tat tat gcg cag cgc gcg cag     192
Ile Pro Asn Arg Asp Trp Ala Val Glu Tyr Tyr Ala Gln Arg Ala Gln
    50                  55                  60 cgc ccg ggc acc ctg att att acc gaa ggc acc ttt ccg agc ccg cag     240
Arg Pro Gly Thr Leu Ile Ile Thr Glu Gly Thr Phe Pro Ser Pro Gln
65                  70                  75 agc ggc ggc tat gat aac gcg ccg ggc att tgg agc gaa gaa cag att     288
Ser Gly Gly Tyr Asp Asn Ala Pro Gly Ile Trp Ser Glu Glu Gln Ile
80                  85                  90                  95 aaa gaa tgg acc aaa att ttt aaa gcg att cat gaa aac aaa agc ttt     336
Lys Glu Trp Thr Lys Ile Phe Lys Ala Ile His Glu Asn Lys Ser Phe
                100                 105                 110 gcg tgg gtg cag ctg tgg gtg ctg ggc tgg gcg gcg ttt ccg gat acc     384
Ala Trp Val Gln Leu Trp Val Leu Gly Trp Ala Ala Phe Pro Asp Thr
            115                 120                 125 ctg gcg cgc gat ggc ctg cgc tat gat agc gcg agc gat aac gtg tat     432
Leu Ala Arg Asp Gly Leu Arg Tyr Asp Ser Ala Ser Asp Asn Val Tyr
        130                 135                 140 atg aac gcg gaa cag gaa gaa aaa gcg aaa aaa gcg aac aac ccg cag     480
Met Asn Ala Glu Gln Glu Glu Lys Ala Lys Lys Ala Asn Asn Pro Gln
    145                 150                 155 cat agc att acc aaa gat gaa att aaa cag tat gtg aaa gaa tat gtg     528
His Ser Ile Thr Lys Asp Glu Ile Lys Gln Tyr Val Lys Glu Tyr Val
160                 165                 170                 175 cag gcg gcg aaa aac agc att gcg gcg ggc gcg gat ggc gtg gaa att     576
Gln Ala Ala Lys Asn Ser Ile Ala Ala Gly Ala Asp Gly Val Glu Ile
                180                 185                 190
```

| | | | | | | | | | | | | | | | |
|---|---|---|---|---|---|---|---|---|---|---|---|---|---|---|---|
| cat | agc | gcg | aac | ggc | tat | ctg | ctg | aac | cag | ttt | ctg | gat | ccg | cat | agc | 624 |
| His | Ser | Ala | Asn | Gly | Tyr | Leu | Leu | Asn | Gln | Phe | Leu | Asp | Pro | His | Ser |
| | | | 195 | | | | | 200 | | | | | 205 | | |

```
cat agc gcg aac ggc tat ctg ctg aac cag ttt ctg gat ccg cat agc      624
His Ser Ala Asn Gly Tyr Leu Leu Asn Gln Phe Leu Asp Pro His Ser
            195                 200                 205 aac aac cgc acc gat gaa tat ggc ggc agc att gaa aac cgc gcg cgc      672
Asn Asn Arg Thr Asp Glu Tyr Gly Gly Ser Ile Glu Asn Arg Ala Arg
        210                 215                 220 ttt acc ctg gaa gtg gtg gat gcg gtg gtg gat gcg att ggc ccg gaa      720
Phe Thr Leu Glu Val Val Asp Ala Val Val Asp Ala Ile Gly Pro Glu
    225                 230                 235 aaa gtg ggc ctg cgc ctg agc ccg tat ggc gtg ttt aac agc atg agc      768
Lys Val Gly Leu Arg Leu Ser Pro Tyr Gly Val Phe Asn Ser Met Ser
240                 245                 250                 255 ggc ggc gcg gaa acc ggc att gtg gcg cag tat gcg tat gtg ctg ggc      816
Gly Gly Ala Glu Thr Gly Ile Val Ala Gln Tyr Ala Tyr Val Leu Gly
            260                 265                 270 gaa ctg gaa cgc cgc gcg aaa gcg ggc aaa cgc ctg gcg ttt gtg cat      864
Glu Leu Glu Arg Arg Ala Lys Ala Gly Lys Arg Leu Ala Phe Val His
        275                 280                 285 ctg gtg gaa ccg cgc gtg acc aac ccg ttt ctg acc gaa ggc gaa ggc      912
Leu Val Glu Pro Arg Val Thr Asn Pro Phe Leu Thr Glu Gly Glu Gly
    290                 295                 300 gaa tat aac ggc ggc agc aac aaa ttt gcg tat agc att tgg aaa ggc      960
Glu Tyr Asn Gly Gly Ser Asn Lys Phe Ala Tyr Ser Ile Trp Lys Gly
305                 310                 315 ccg att att cgc gcg ggc aac ttt gcg ctg cat ccg gaa gtg gtg cgc     1008
Pro Ile Ile Arg Ala Gly Asn Phe Ala Leu His Pro Glu Val Val Arg
320                 325                 330                 335 gaa gaa gtg aaa gat ccg cgc acc ctg att ggc tat ggc cgc ttt ttt     1056
Glu Glu Val Lys Asp Pro Arg Thr Leu Ile Gly Tyr Gly Arg Phe Phe
            340                 345                 350 att agc aac ccg gat ctg gtg gat cgc ctg gaa aaa ggc ctg ccg ctg     1104
Ile Ser Asn Pro Asp Leu Val Asp Arg Leu Glu Lys Gly Leu Pro Leu
        355                 360                 365 aac aaa tat gat cgc gat acc ttt tat aaa atg agc gcg gaa ggc tat     1152
Asn Lys Tyr Asp Arg Asp Thr Phe Tyr Lys Met Ser Ala Glu Gly Tyr
    370                 375                 380 att gat tat ccg acc tat gaa gaa gcg ctg aaa ctg ggc tgg gat aaa     1200
Ile Asp Tyr Pro Thr Tyr Glu Glu Ala Leu Lys Leu Gly Trp Asp Lys
385                 390                 395 aac atgacttaac tgcagccaag cttggctgtt ttggcggatg agagaagatt          1253
Asn
400 ttcagcctga tacagattaa atcagaacgc agaagcggtc tgataaaaca gaatttgcct   1313 ggcggcagta gcgcggtggt cccacctgac cccatgccga actcagaagt gaaacgccgt   1373 agcgccgatg gtagtgtggg gtctccccat gcgagagtag ggaactgcca ggcatcaaat   1433 aaaacgaaag gctcagtcga agactgggcc tttcgttttt atctgttgtt tgtcggtgaa   1493 cgctctcctg agtaggacaa atccgccggg agcggatttg aacgttgcga agcaacggcc   1553 cggagggtgg cgggcaggac gcccgccata aactgccagg catcaaatta agcagaaggc   1613 catcctgacg gatggccttt ttgcgtttct acaaactctt tgtttatttt tctaaatac    1673 attcaaatat gtatccgctc atgagacaat aaccctgata atgcttcaa taatattgaa    1733 aaggaagagt atgagtattc aacatttccg tgtcgccctt attccctttt tgcggcatt    1793 ttgccttcct gttttgctc acccagaaac gctggtgaaa gtaaaagatg ctgaagatca    1853 gttgggtgca cgagtgggtt acatcgaact ggatctcaac agcggtaaga tccttgagag   1913 ttttcgcccc gaagaacgtt ttccaatgat gagcactttt aaagttctgc tatgtggcgc   1973
```

```
ggtattatcc cgtgttgacg ccgggcaaga gcaactcggt cgccgcatac actattctca   2033
gaatgacttg gttgagtact caccagtcac agaaaagcat cttacggatg gcatgacagt   2093
aagagaatta tgcagtgctg ccataaccat gagtgataac actgcggcca acttacttct   2153
gacaacgatc ggaggaccga aggagctaac cgcttttttg cacaacatgg gggatcatgt   2213
aactcgcctt gatcgttggg aaccggagct gaatgaagcc ataccaaacg acgagcgtga   2273
caccacgatg cctgtagcaa tggcaacaac gttgcgcaaa ctattaactg gcgaactact   2333
tactctagct tcccggcaac aattaataga ctggatggag gcggataaag ttgcaggacc   2393
acttctgcgc tcggcccttc cggctggctg gtttattgct gataaatctg gagccggtga   2453
gcgtgggtct cgcggtatca ttgcagcact ggggccagat ggtaagccct cccgtatcgt   2513
agttatctac acgacgggga gtcaggcaac tatggatgaa cgaaatagac agatcgctga   2573
gataggtgcc tcactgatta agcattggta actgtcagac caagtttact catatatact   2633
ttagattgat ttaaaacttc attttttaatt taaaaggatc taggtgaaga tcctttttga   2693
taatctcatg accaaaatcc cttaacgtga gttttcgttc cactgagcgt cagacccgt    2753
agaaaagatc aaaggatctt cttgagatcc ttttttttctg cgcgtaatct gctgcttgca   2813
aacaaaaaaa ccaccgctac cagcggtggt ttgtttgccg gatcaagagc taccaactct   2873
ttttccgaag gtaactggct tcagcagagc gcagatacca aatactgtcc ttctagtgta   2933
gccgtagtta ggccaccact tcaagaactc tgtagcaccg cctacatacc tcgctctgct   2993
aatcctgtta ccagtggctg ctgccagtgg cgataagtcg tgtcttaccg ggttggactc   3053
aagacgatag ttaccggata aggcgcagcg gtcgggctga acggggggtt cgtgcacaca   3113
gcccagcttg gagcgaacga cctacaccga actgagatac ctacagcgtg agctatgaga   3173
aagcgccacg cttcccgaag ggagaaaggc ggacaggtat ccggtaagcg cagggtcgg    3233
aacaggagag cgcacgaggg agcttccagg gggaaacgcc tggtatcttt atagtcctgt   3293
cgggtttcgc cacctctgac ttgagcgtcg attttttgtga tgctcgtcag ggggggcggag  3353
cctatggaaa aacgccagca acgcggcctt tttacggttc ctggccttttt gctggccttt   3413
tgctcacatg ttctttcctg cgttatcccc tgattctgtg gataaccgta ttaccgcctt   3473
tgagtgagct gataccgctc gccgcagccg aacgaccgag cgcagcgagt cagtgagcga   3533
ggaagcggaa gagcgcctga tgcggtattt tctccttacg catctgtgcg gtatttcaca   3593
ccgcatatat ggtgcactct cagtacaatc tgctctgatg ccgcatagtt aagccagtat   3653
acactccgct atcgctacgt gactgggtca tggctgcgcc ccgacacccg ccaacacccg   3713
ctgacgcgcc ctgacgggct tgtctgctcc cggcatccgc ttacagacaa gctgtgaccg   3773
tctccgggag ctgcatgtgt cagaggtttt caccgtcatc accgaaacgc gcgaggcagc   3833
tgcggtaaag ctcatcagcg tggtcgtgaa gcgattcaca gatgtctgcc tgttcatccg   3893
cgtccagctc gttgagtttc tccagaagcg ttaatgtctg gcttctgata aagcgggcca   3953
tgttaagggc ggttttttcc tgtttggtca cttgatgcct ccgtgtaagg gggaatttct   4013
gttcatgggg gtaatgatac cgatgaaacg agagaggatg ctcacgatac gggttactga   4073
tgatgaacat gcccggttac tggaacgttg tgagggtaaa caactggcgg tatggatgcg   4133
gcgggaccag agaaaaatca ctcagggtca atgccacgc ttcgttaata cagatgtagg    4193
tgttccacag ggtagccagc agcatcctgc gatgcagatc cggaacataa tggtgcaggg   4253
cgctgacttc gcgtttccac gactttacga aacacgaaa ccgaagacca ttcatgttgt    4313
tgctcaggtc gcagacgttt tgcagcagca gtcgcttcac gttcgctcgc gtatcggtga   4373
```

```
ttcattctgc taaccagtaa ggcaaccccg ccagcctagc cgggtcctca acgacaggag   4433
cacgatcatg cgcacccgtg ccaggaccca acgctgccc gagatgcgcc gcgtgcggct    4493
gctggagatg cgcgacgcga tggatatgtt ctgccaaggg ttggtttgcg cattcacagt   4553
tctccgcaag aattgattgg ctccaattct tggagtggtg aatccgttag cgaggtgccg   4613
ccggcttcca ttcaggtcga ggtggcccgg ctccatgcac cgcgacgcaa cgcggggagg   4673
cagacaaggt atagggcggc gcctacaatc catgccaacc cgttccatgt gctcgccgag   4733
gcggcataaa tcgccgtgac gatcagcggt ccagtgatcg aagttaggct ggtaagagcc   4793
gcgagcgatc cttgaagctg tccctgatgg tcgtcatcta cctgcctgga cagcatggcc   4853
tgcaacgcgg gcatcccgat gccgccggaa gcgagaagaa tcataatggg gaaggccatc   4913
cagcctcgcg tcgcgaacgc cagcaagacg tagcccagcc cgtcggccgc catgccggcg   4973
ataatggcct gcttctcgcc gaaacgtttg gtggcgggac cagtgacgaa ggcttgagcg   5033
agggcgtgca agattccgaa taccgcaagc gacaggccga tcatcgtcgc gctccagcga   5093
aagcggtcct cgccgaaaat gacccagagc gctgccggca cctgtcctac gagttgcatg   5153
ataaagaaga cagtcataag tgcggcgacg atagtcatgc cccgcgccca ccggaaggag   5213
ctgactgggt tgaaggctct caagggcatc ggtcgacgct ctcccttatg cgactcctgc   5273
attaggaagc agcccagtag taggttgagg ccgttgagca ccgccgccgc aaggaatggt   5333
gcatgcatcg atcaccacaa ttcagcaaat tgtgaacatc atcacgttca tctttccctg   5393
gttgccaatg gcccattttc ctgtcagtaa cgagaaggtc gcgaattcag gcgcttttta   5453
gactggtcgt aatgaacaat tcttaagaag gagatata                          5491
```

<210> SEQ ID NO 7
<211> LENGTH: 400
<212> TYPE: PRT
<213> ORGANISM: Artificial
<220> FEATURE:
<223> OTHER INFORMATION: Synthetic Construct

<400> SEQUENCE: 7

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
                20                  25                  30

Val Ile Pro Pro Leu Thr Arg Met Arg Ala Gln His Pro Gly Asn Ile
            35                  40                  45

Pro Asn Arg Asp Trp Ala Val Glu Tyr Tyr Ala Gln Arg Ala Gln Arg
        50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
                100                 105                 110

Trp Val Gln Leu Trp Val Leu Gly Trp Ala Ala Phe Pro Asp Thr Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln

```
                            165                 170                 175
Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
            210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
                275                 280                 285

Val Glu Pro Arg Val Thr Asn Pro Phe Leu Thr Glu Gly Glu Gly Glu
            290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
            355                 360                 365

Lys Tyr Asp Arg Asp Thr Phe Tyr Lys Met Ser Ala Glu Gly Tyr Ile
            370                 375                 380

Asp Tyr Pro Thr Tyr Glu Glu Ala Leu Lys Leu Gly Trp Asp Lys Asn
385                 390                 395                 400

<210> SEQ ID NO 8
<211> LENGTH: 5474
<212> TYPE: DNA
<213> ORGANISM: Artificial
<220> FEATURE:
<223> OTHER INFORMATION: Plasmid encoding OYE3
<220> FEATURE:
<221> NAME/KEY: CDS
<222> LOCATION: (4)..(1203)

<400> SEQUENCE: 8 cat atg ccg ttt gtg aaa ggc ttt gaa ccg att agc ctg cgc gat acc      48
    Met Pro Phe Val Lys Gly Phe Glu Pro Ile Ser Leu Arg Asp Thr
    1               5                   10                  15 aac ctg ttt gaa ccg att aaa att ggc aac acc cag ctg gcg cat cgc      96
Asn Leu Phe Glu Pro Ile Lys Ile Gly Asn Thr Gln Leu Ala His Arg
                20                  25                  30 gcg gtg atg ccg ccg ctg acc cgc atg cgc gcg acc cat ccg ggc aac     144
Ala Val Met Pro Pro Leu Thr Arg Met Arg Ala Thr His Pro Gly Asn
            35                  40                  45 att ccg aac aaa gaa tgg gcg gcg gtg tat tat ggc cag cgc gcg cag     192
Ile Pro Asn Lys Glu Trp Ala Ala Val Tyr Tyr Gly Gln Arg Ala Gln
        50                  55                  60 cgc ccg ggc acc atg att att acc gaa ggc acc ttt att agc ccg cag     240
Arg Pro Gly Thr Met Ile Ile Thr Glu Gly Thr Phe Ile Ser Pro Gln
65                  70                  75 gcg ggc ggc tat gat aac gcg ccg ggc att tgg agc gat gaa cag gtg     288
Ala Gly Gly Tyr Asp Asn Ala Pro Gly Ile Trp Ser Asp Glu Gln Val
80                  85                  90                  95
```

| | | |
|---|---|---|
| gcg gaa tgg aaa aac att ttt ctg gcg att cat gat tgc cag agc ttt<br>Ala Glu Trp Lys Asn Ile Phe Leu Ala Ile His Asp Cys Gln Ser Phe<br>              100                        105                    110 | 336 | |
| gcg tgg gtg cag ctg tgg agc ctg ggc tgg gcg agc ttt ccg gat gtg<br>Ala Trp Val Gln Leu Trp Ser Leu Gly Trp Ala Ser Phe Pro Asp Val<br>              115                        120                    125 | 384 | |
| ctg gcg cgc gat ggc ctg cgc tat gat tgc gcg agc gat cgc gtg tat<br>Leu Ala Arg Asp Gly Leu Arg Tyr Asp Cys Ala Ser Asp Arg Val Tyr<br>              130                        135                    140 | 432 | |
| atg aac gcg acc ctg cag gaa aaa gcg aaa gat gcg aac aac ctg gaa<br>Met Asn Ala Thr Leu Gln Glu Lys Ala Lys Asp Ala Asn Asn Leu Glu<br>145                        150                        155 | 480 | |
| cat agc ctg acc aaa gat gat att aaa cag tat att aaa gat tat att<br>His Ser Leu Thr Lys Asp Asp Ile Lys Gln Tyr Ile Lys Asp Tyr Ile<br>160                        165                        170                    175 | 528 | |
| cat gcg gcg aaa aac agc att gcg gcg ggc gcg gat ggc gtg gaa att<br>His Ala Ala Lys Asn Ser Ile Ala Ala Gly Ala Asp Gly Val Glu Ile<br>                    180                        185                    190 | 576 | |
| cat agc gcg aac ggc tat ctg ctg aac cag ttt ctg gat ccg cat agc<br>His Ser Ala Asn Gly Tyr Leu Leu Asn Gln Phe Leu Asp Pro His Ser<br>              195                        200                    205 | 624 | |
| aac aaa cgc acc gat gaa tat ggc ggc acc att gaa aac cgc gcg cgc<br>Asn Lys Arg Thr Asp Glu Tyr Gly Gly Thr Ile Glu Asn Arg Ala Arg<br>                210                        215                    220 | 672 | |
| ttt acc ctg gaa gtg gtg gat gcg ctg att gaa acc att ggc ccg gaa<br>Phe Thr Leu Glu Val Val Asp Ala Leu Ile Glu Thr Ile Gly Pro Glu<br>        225                        230                        235 | 720 | |
| cgc gtg ggc ctg cgc ctg agc ccg tat ggc acc ttt aac agc atg agc<br>Arg Val Gly Leu Arg Leu Ser Pro Tyr Gly Thr Phe Asn Ser Met Ser<br>240                        245                        250                    255 | 768 | |
| ggc ggc gcg gaa ccg ggc att att gcg cag tat agc tat gtg ctg ggc<br>Gly Gly Ala Glu Pro Gly Ile Ile Ala Gln Tyr Ser Tyr Val Leu Gly<br>                    260                        265                    270 | 816 | |
| gaa ctg gaa aaa cgc gcg aaa gcg ggc aaa cgc ctg gcg ttt gtg cat<br>Glu Leu Glu Lys Arg Ala Lys Ala Gly Lys Arg Leu Ala Phe Val His<br>              275                        280                    285 | 864 | |
| ctg gtg gaa ccg cgc gtg acc gat ccg agc ctg gtg gaa ggc gaa ggc<br>Leu Val Glu Pro Arg Val Thr Asp Pro Ser Leu Val Glu Gly Glu Gly<br>                290                        295                    300 | 912 | |
| gaa tat agc gaa ggc acc aac gat ttt gcg tat agc att tgg aaa ggc<br>Glu Tyr Ser Glu Gly Thr Asn Asp Phe Ala Tyr Ser Ile Trp Lys Gly<br>        305                        310                        315 | 960 | |
| ccg att att cgc gcg ggc aac tat gcg ctg cat ccg gaa gtg gtg cgc<br>Pro Ile Ile Arg Ala Gly Asn Tyr Ala Leu His Pro Glu Val Val Arg<br>320                        325                        330                    335 | 1008 | |
| gaa cag gtg aaa gat ccg cgc acc ctg att ggc tat ggc cgc ttt ttt<br>Glu Gln Val Lys Asp Pro Arg Thr Leu Ile Gly Tyr Gly Arg Phe Phe<br>                    340                        345                    350 | 1056 | |
| att agc aac ccg gat ctg gtg tat cgc ctg gaa gaa ggc ctg ccg ctg<br>Ile Ser Asn Pro Asp Leu Val Tyr Arg Leu Glu Glu Gly Leu Pro Leu<br>              355                        360                    365 | 1104 | |
| aac aaa tat gat cgc agc acc ttt tat acc atg agc gcg gaa ggc tat<br>Asn Lys Tyr Asp Arg Ser Thr Phe Tyr Thr Met Ser Ala Glu Gly Tyr<br>          370                        375                    380 | 1152 | |
| acc gat tat ccg acc tat gaa gaa gcg gtg gat ctg ggc tgg aac aaa<br>Thr Asp Tyr Pro Thr Tyr Glu Glu Ala Val Asp Leu Gly Trp Asn Lys<br>385                        390                        395 | 1200 | |
| aac aagcttggct gttttggcgg atgagagaag attttcagcc tgatacagat<br>Asn<br>400 | 1253 | |

-continued

```
taaatcagaa cgcagaagcg gtctgataaa acagaatttg cctggcggca gtagcgcggt    1313
ggtcccacct gaccccatgc cgaactcaga agtgaaacgc cgtagcgccg atggtagtgt    1373
ggggtctccc catgcgagag tagggaactg ccaggcatca aataaaacga aaggctcagt    1433
cgaaagactg ggcctttcgt tttatctgtt gtttgtcggt gaacgctctc ctgagtagga    1493
caaatccgcc gggagcggat ttgaacgttg cgaagcaacg gcccggaggg tggcgggcag    1553
gacgcccgcc ataaactgcc aggcatcaaa ttaagcagaa ggccatcctg acggatggcc    1613
tttttgcgtt tctacaaact cttttgttta tttttctaaa tacattcaaa tatgtatccg    1673
ctcatgagac aataaccctg ataaatgctt caataatatt gaaaaggaag agtatgagta    1733
ttcaacattt ccgtgtcgcc cttattccct ttttttgcgg cattttgcctt cctgtttttg    1793
ctcacccaga aacgctggtg aaagtaaaag atgctgaaga tcagttgggt gcacgagtgg    1853
gttacatcga actggatctc aacagcggta agatccttga gttttcgc cccgaagaac    1913
gttttccaat gatgagcact tttaaagttc tgctatgtgg cgcggtatta tcccgtgttg    1973
acgccgggca agagcaactc ggtcgccgca tacactattc tcagaatgac ttggttgagt    2033
actcaccagt cacagaaaag catcttacgg atggcatgac agtaagagaa ttatgcagtg    2093
ctgccataac catgagtgat aacactgcgg ccaacttact tctgacaacg atcggaggac    2153
cgaaggagct aaccgctttt ttgcacaaca tgggggatca tgtaactcgc cttgatcgtt    2213
gggaaccgga gctgaatgaa gccataccaa acgacgagcg tgacaccacg atgcctgtag    2273
caatggcaac aacgttgcgc aaactattaa ctggcgaact acttactcta gcttcccggc    2333
aacaattaat agactggatg gaggcggata agttgcagg accacttctg cgctcggccc    2393
ttccggctgg ctggtttatt gctgataaat ctggagccgg tgagcgtggg tctcgcggta    2453
tcattgcagc actggggcca gatggtaagc cctcccgtat cgtagttatc tacacgacgg    2513
ggagtcaggc aactatggat gaacgaaata gacagatcgc tgagataggt gcctcactga    2573
ttaagcattg gtaactgtca gaccaagttt actcatatat actttagatt gatttaaaac    2633
ttcatttta atttaaaagg atctaggtga agatccttt tgataatctc atgaccaaaa    2693
tcccttaacg tgagttttcg ttccactgag cgtcagaccc cgtagaaaag atcaaaggat    2753
cttcttgaga tcctttttt ctgcgcgtaa tctgctgctt gcaaacaaaa aaaccaccgc    2813
taccagcggt ggtttgtttg ccggatcaag agctaccaac tcttttccg aaggtaactg    2873
gcttcagcag agcgcagata ccaaatactg tccttctagt gtagccgtag ttaggccacc    2933
acttcaagaa ctctgtagca ccgcctacat acctcgctct gctaatcctg ttaccagtgg    2993
ctgctgccag tggcgataag tcgtgtctta ccgggttgga ctcaagacga tagttaccgg    3053
ataaggcgca gcggtcgggc tgaacggggg gttcgtgcac acagcccagc ttggagcgaa    3113
cgacctacac cgaactgaga tacctacagc gtgagctatg agaaagcgcc acgcttcccg    3173
aagggagaaa ggcggacagg tatccggtaa gcggcagggt cggaacagga gagcgcacga    3233
gggagcttcc agggggaaac gcctggtatc tttatagtcc tgtcgggttt cgccacctct    3293
gacttgagcg tcgatttttg tgatgctcgt caggggggcg gagcctatgg aaaaacgcca    3353
gcaacgcggc cttttttacgg ttcctggcct tttgctggcc ttttgctcac atgttctttc    3413
ctgcgttatc ccctgattct gtggataacc gtattaccgc ctttgagtga gctgataccg    3473
ctcgccgcag ccgaacgacc gagcgcagcg agtcagtgag cgaggaagcg gaagagcgcc    3533
tgatgcggta ttttctcctt acgcatctgt gcggtatttc acaccgcata tatggtgcac    3593
tctcagtaca atctgctctg atgccgcata gttaagccag tatacactcc gctatcgcta    3653
```

```
cgtgactggg tcatggctgc gccccgacac ccgccaacac ccgctgacgc gccctgacgg    3713
gcttgtctgc tcccggcatc cgcttacaga caagctgtga ccgtctccgg agctgcatg    3773 tgtcagaggt tttcaccgtc ataccgaaa cgcgcgaggc agctgcggta aagctcatca    3833
gcgtggtcgt gaagcgattc acagatgtct gcctgttcat ccgcgtccag ctcgttgagt    3893
ttctccagaa gcgttaatgt ctggcttctg ataaagcggg ccatgttaag ggcggttttt    3953
tcctgtttgg tcacttgatg cctccgtgta agggggaatt tctgttcatg ggggtaatga    4013
taccgatgaa acgagagagg atgctcacga tacgggttac tgatgatgaa catgcccggt    4073
tactggaacg ttgtgagggt aaacaactgg cggtatggat gcggcgggac cagagaaaaa    4133
tcactcaggg tcaatgccag cgcttcgtta atacagatgt aggtgttcca cagggtagcc    4193
agcagcatcc tgcgatgcag atccggaaca taatggtgca gggcgctgac ttccgcgttt    4253
ccagacttta cgaaacacgg aaaccgaaga ccattcatgt tgttgctcag gtcgcagacg    4313
ttttgcagca gcagtcgctt cacgttcgct cgcgtatcgg tgattcattc tgctaaccag    4373
taaggcaacc ccgccagcct agccgggtcc tcaacgacag gagcacgatc atgcgcaccc    4433
gtggccagga cccaacgctg cccgagatgc ccgcgtgcg gctgctggag atggcggacg    4493
cgatggatat gttctgccaa gggttggttt gcgcattcac agttctccgc aagaattgat    4553
tggctccaat tcttggagtg gtgaatccgt tagcgaggtg ccgccggctt ccattcaggt    4613
cgaggtggcc cggctccatg caccgcgacg caacgcgggg aggcagacaa ggtatagggc    4673
ggcgcctaca atccatgcca acccgttcca tgtgctcgcc gaggcggcat aaatcgccgt    4733
gacgatcagc ggtccagtga tcgaagttag gctggtaaga gccgcgagcg atccttgaag    4793
ctgtccctga tggtcgtcat ctacctgcct ggacagcatg gcctgcaacg cgggcatccc    4853
gatgccgccg gaagcgagaa gaatcataat ggggaaggcc atccagcctc gcgtcgcgaa    4913
cgccagcaag acgtagccca gcgcgtcggc cgccatgccg gcgataatgg cctgcttctc    4973
gccgaaacgt ttggtggcgg gaccagtgac gaaggcttga gcgagggcgt gcaagattcc    5033
gaataccgca agcgacaggc cgatcatcgt cgcgctccag cgaaagcggt cctcgccgaa    5093
aatgacccag agcgctgccg gcacctgtcc tacgagttgc atgataaaga agacagtcat    5153
aagtgcggcg acgatagtca tgccccgcgc ccaccggaag gagctgactg ggttgaaggc    5213
tctcaagggc atcggtcgac gctctccctt atgcgactcc tgcattagga agcagcccag    5273
tagtaggttg aggccgttga gcaccgccgc cgcaaggaat ggtgcatgca tcgatcacca    5333
caattcagca aattgtgaac atcatcacgt tcatctttcc ctggttgcca atggcccatt    5393
ttcctgtcag taacgagaag gtcgcgaatt caggcgcttt ttagactggt cgtaatgaac    5453
aattcttaag aaggagatat a                                              5474
```

<210> SEQ ID NO 9
<211> LENGTH: 400
<212> TYPE: PRT
<213> ORGANISM: Artificial
<220> FEATURE:
<223> OTHER INFORMATION: Synthetic Construct

<400> SEQUENCE: 9

```
Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
```

```
                35                  40                  45
Pro Asn Lys Glu Trp Ala Ala Val Tyr Tyr Gly Gln Arg Ala Gln Arg
 50                  55                  60

Pro Gly Thr Met Ile Ile Thr Glu Gly Thr Phe Ile Ser Pro Gln Ala
 65                  70                  75                  80

Gly Gly Tyr Asp Asn Ala Pro Gly Ile Trp Ser Asp Glu Gln Val Ala
                 85                  90                  95

Glu Trp Lys Asn Ile Phe Leu Ala Ile His Asp Cys Gln Ser Phe Ala
                100                 105                 110

Trp Val Gln Leu Trp Ser Leu Gly Trp Ala Ser Phe Pro Asp Val Leu
                115                 120                 125

Ala Arg Asp Gly Leu Arg Tyr Asp Cys Ala Ser Asp Arg Val Tyr Met
130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
                195                 200                 205

Lys Arg Thr Asp Glu Tyr Gly Gly Thr Ile Glu Asn Arg Ala Arg Phe
210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
                260                 265                 270

Leu Glu Lys Arg Ala Lys Ala Gly Lys Arg Leu Ala Phe Val His Leu
                275                 280                 285

Val Glu Pro Arg Val Thr Asp Pro Ser Leu Val Glu Gly Glu Gly Glu
                290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
                370                 375                 380

Asp Tyr Pro Thr Tyr Glu Glu Ala Val Asp Leu Gly Trp Asn Lys Asn
385                 390                 395                 400
```